United States Patent [19]

Khanna et al.

[11] Patent Number: 4,834,111

[45] Date of Patent: May 30, 1989

[54] HETERODYNE INTERFEROMETER

[75] Inventors: S. M. Khanna, Somerset, N.J.; J. F. Willemin, Wernetshausen; R. Dandliker, Corcelles, both of Switzerland

[73] Assignee: The Trustees of Columbia University in the City of New York, New York, N.Y.

[21] Appl. No.: 2,149

[22] Filed: Jan. 12, 1987

[51] Int. Cl.⁴ ................................................ A61B 5/10
[52] U.S. Cl. ..................................... 128/774; 356/351; 73/657
[58] Field of Search ................... 128/774, 782; 73/655, 73/657; 356/350, 351, 357

[56] References Cited

U.S. PATENT DOCUMENTS

| | | | |
|---|---|---|---|
| 4,172,382 | 10/1979 | Murphy et al. | 73/655 |
| 4,208,128 | 6/1980 | Thompson et al. | 356/350 |
| 4,422,764 | 12/1983 | Eastman | 356/357 |
| 4,554,836 | 11/1985 | Rudd | 73/657 |
| 4,643,575 | 2/1987 | Hazeltine et al. | 356/361 |
| 4,681,447 | 7/1987 | Davidsen | 356/351 |

Primary Examiner—Max Hindenburg
Attorney, Agent, or Firm—John P. White

[57] ABSTRACT

This invention concerns a heterodyne interferometer for measuring the amplitude of vibration of a vibrating object. The invention is particularly useful for measuring the amplitude of vibrations of objects having reflectivities below about 0.02% or for measuring vibrations amplitudes below about $10^{-17}$ cm.

The invention comprises a laser and a beam splitter for producing an object light wave and a reference light wave; at least one modulator for changing the frequencies of the object light wave and the reference light wave thereby producing a predetermined offset; means for directing the object light wave onto the vibrating object; and a photodetector for producing, at a frequency equal to the predetrmined offset, a beat signal which varies according to variations in the interference resulting from combining the reflected object light wave and the reference light wave.

14 Claims, 17 Drawing Sheets

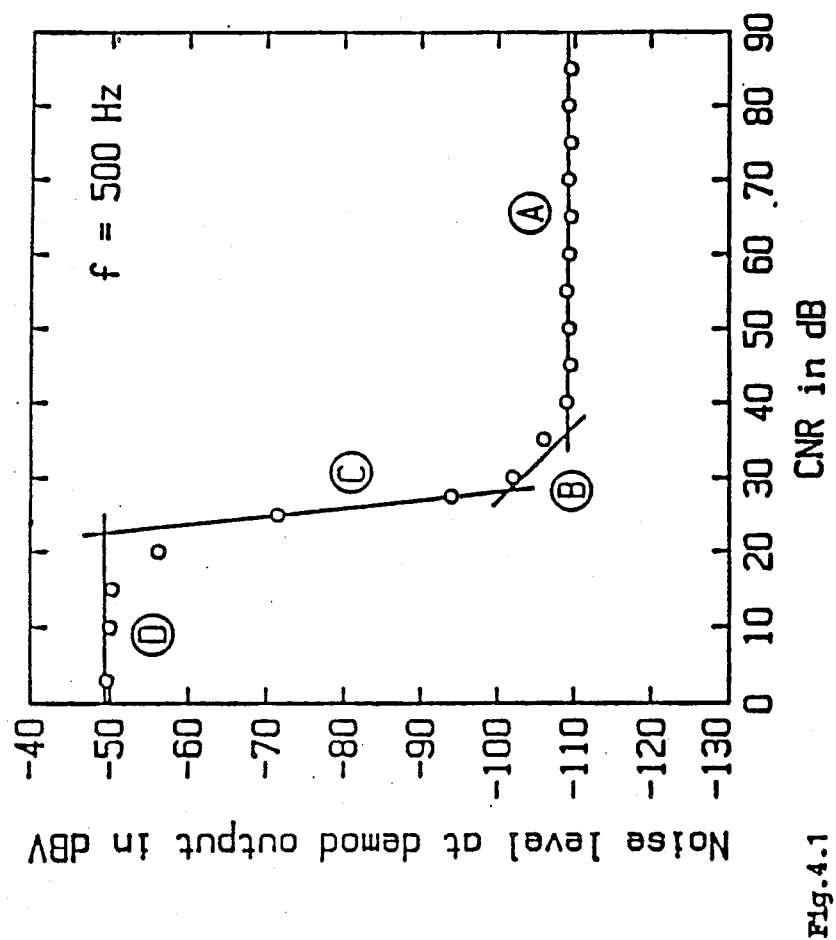
Fig. 4.1

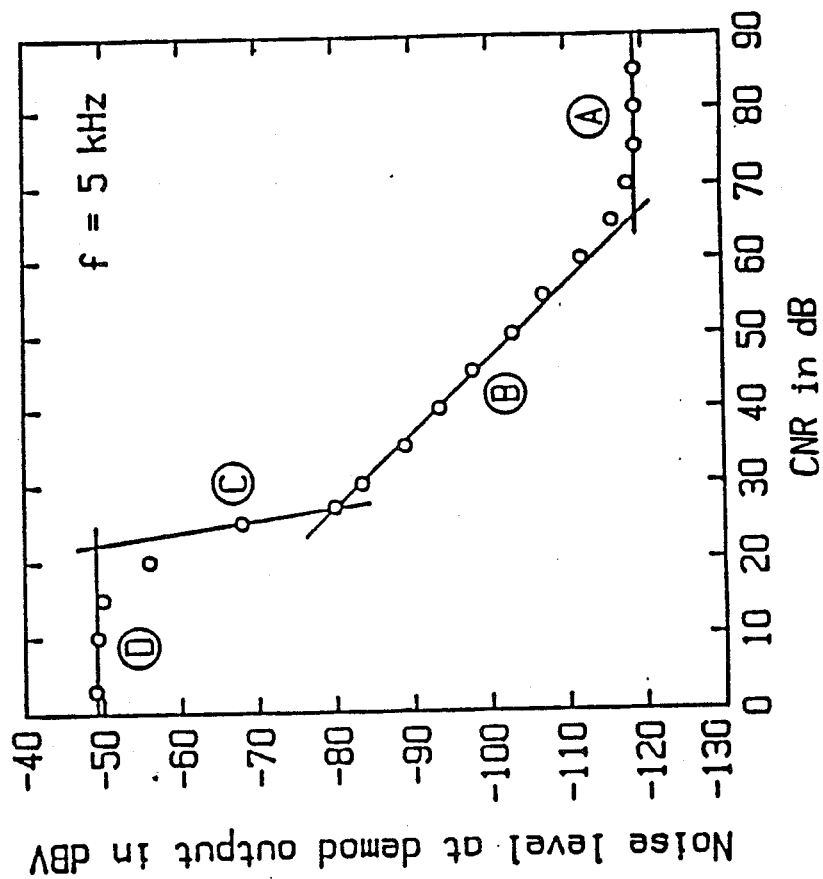
Fig. 4.2

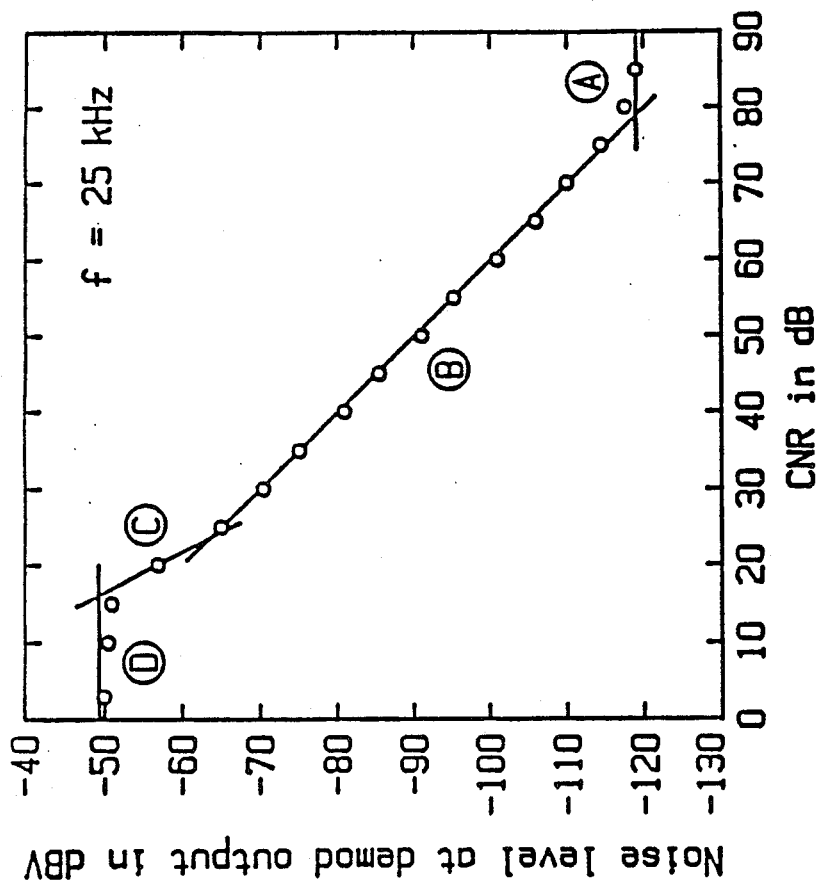
Fig.4.3

HETERODYNE INTERFEROMETER

BACKGROUND OF THE INVENTION

The invention described herein was made in the course of work under Grant No. 84-13419 from the National Science Foundation. The U.S. Government has certain rights in this invention.

Within this application several publications are referenced by Arabic numerals within brackets. Full citations for these references may be found at the end of the specification immediately preceding the claims. The disclosures of these publications in their entirety are hereby incorporated by reference into this application in order to more fully describe the state of the art to which this invention pertains.

At present, inner ear vibration measurement techniques require opening the cochlea. These include (i) Mossbauer, (ii) capacitive probe, and (iii) interferometric methods. In the Mossbauer method the cohclear opening is needed in order to place a radioactive foil on the membrane whose vibration is to be measured [1-14]. In the capacitive probe method the cochlea is opened in order to place the probe close to the basilar membrane [15-17]. In the interferometric techniques the cochlea is opened to place a mirror on the basilar membrane [18,19], or to bring the fiber optic probe near the basilar memrane [20, 21]. In one interferometric technique the cochlea is opened to cement a glass window [22].

There are serious problems with the use of techniques which require surgical opening of the cochlea. Damage is incurred to the cochlea in the opening process and once the cochlea is opened damage increases with time [14,17,23-26]. Another problem with these techniques is that the surface to be measured must be accessible from outside. This limits the measurements to basilar and Reisners membrane. Due to the finite size of the Mossbauer source, the mirrors and the capacitive probe tip, measurements must be made on areas no smaller than (50 μm)$^2$.

Conditions in the inner ear for interferometric measurements are quite different than those encountered in other mechanical systems: (i) The inner ear is mechanically not stable, due to blood pulsations and breathing artifacts; (ii) access to the inner ear is limited by anatomical constraints making it difficult to visualize the structures of interest; (iii) vibration amplitudes to be measured in the inner ear are very low; (v) the structures in the inner ear are nearly transparent therefore the reflectivity is low, attempts to change this reflectivity artificially usually alters the response characteristics; (vi) cells are subject to light damage if the incident light intensity is too high. This limits the laser power that can be utilized in the interferometer.

Methods have been described which apply homodyne interferometry to vibration measurements in the middle ear [44] and in the inner ear [45,18]. The theory, hardware and techniques of the homodyne interferometer utilized in these methods have been recently described [43,48]. The sensitivity of the homodyne method drops steeply with the reduction of signal light intensity. To obtain high reflectivity, tiny gold mirrors are placed on the basilar membrane. This method however will not be suitable when vibration measurements are made in cochleas without mirror placements in which case the reflectivities drop to about 0.02% of the values obtained with mirrors placed on the basilar membrane.

The present invention can measure at low light levels, while still retaining a measurement sensitivity of at least $10^{-9}$ cm. The interferometry technique of the present invention utilizes the heterodyne method in order to improve the signal-to-noise ratio in the system.

In this method, a laser beam is split into two parts. The frequencies of the resulting beams are shifted by a fixed amount $\Delta\omega$ by frequency shifters. One beam is then directed onto the object whose vibrations are to be measured. The reflected and/or scattered beam from the object is mixed with the other beam in a photodetector. When the object is stationary, the interference between the two beams results in a detector output at the beat frequency $\Delta\omega$. When the object vibrates, the frequency of the reflected beam is frequency modulated due to the Doppler effect. The detector output then consists of a beat which is frequency-modulated. The object motion can be measured by demodulating the detector output with an FM-demodulator centered at the beat frequency.

The following advantages of heterodyne interferometry are evident in comparison with classical (homodyne) interferometry [35,36]. First, in contrast to homodyne techniques, the linearity of heterodyne interferometry is not limited to small vibration amplitudes, because optical phase variations are not converted to intensity variations (according to a sine function) but to phase variations of an electrical ac signal at the beat frequency. Therefore, this technique is well suited to study nonlinear effects. Second, the familiar quadrature condition which has to be maintained for homodyne techniques is not necessary with heterodyning, because sensitivity is essentially independent of the phase difference between the two interfering beams. In heterodyne interferometry, the interference phase is completely separated from the interference amplitude and from the other terms resulting from the super-position of the two fields. Therefore, drifts taking the interferometer away from the quadrature condition does not cause signal fading. Thus, problems with the position control of the reference mirror are avoided, and the reference beam path can be completely outside the system under study. The property is particularly important for investigations on biological systems. Finally, heterodyne interferometry does not need a vibrating reference mirror for calibration, because the interference phase, which is proportional to the displacement to be measured depends only on the geometry of the illumination and reflection (and of course also on the wavelength λ).

SUMMARY OF THE INVENTION

This invention concerns a heterodyne interferometer for measuring the amplitude of vibration of a vibrating object. The interferometer comprises:

(a) a laser for emitting a monochromatic light wave;

(b) a beam splitter for splitting the light wave into an object light wave and a reference light wave, each having the same frequency;

(c) a modulator for changing the frequency of the object light wave and the reference light wave so as to produce a predetermined offset between the frequency of the object light wave and the frequency of the reference light wave, said modulator being so positioned with respect to the beam splitter that the object light wave and the reference light wave pass through the modulator thereby changing their frequencies;

(d) means for directing the object light wave onto the vibrating object, said means so positioned between the object and the modulator that at least a portion of the object light wave is directed onto and reflected off of the object;

(e) a photodetector for producing, at a frequency equal to the predetermined offset, a beat signal varying in accordance with variations in the interference resulting from combining at least a portion of the reflected object light wave and the reference light wave, the photodetector being so positioned with respect to the object and the beam splitter that it detects and measures the interference; and (f) means for processing the beat signal to measure variations in its phase or amplitude, said means being electrically connected to the photodetector in order to receive the beat signal.

The invention also provides a method for measuring the amplitude of vibration of a vibrating object. In one embodiment, the method comprises using the heterodyne interferometer of this invention. In another embodiment, the method comprises:

(a) generating a monochromatic light wave;

(b) splitting the light wave into an object light wave and a reference light wave;

(c) changing the frequencies of the object light wave and the reference light wave by passing the object light wave and the reference light wave through a modulator to produce a predetermined offset between the frequencies of the object light wave and the reference light wave;

(d) directing the object light wave onto the vibrating object so that at least a portion of the object light wave is reflected by the object;

(e) combining at least a portion of the reflected object light wave and the reference light wave to form an interference;

(f) measuring the interference in such a manner so as to produce a beat signal at a frequency equal to the predetermined offset having variations corresponding to variations in the interference; and (g) processing the beat signal so as to measure variations in its phase or amplitude.

BRIEF DESCRIPTION OF THE FIGURES

FIGS. 4. Demodulator output noise level as a function of CNR. The measurement bandwidth is 1.5 Hz for the demodulator noise and 3 kHz for the CNR. Measurements are shown for three different vibration frequencies: 500 Hz, 5 kHz and 25 kHz in FIGS. 4.1, 4.2 and 4.3, respectively. The curves show four distinct slopes: A, B, C and D.

A laser beam reflected by the mirror $M_1$ is split into two parts by a beam splitter $BS_1$. The object beam reflected by the mirror $M_2$ is frequency shifted (45 mHz) by the acousto-optic modulator $AOM_2$ and attenuated by the attenuator $ATT_2$. The aperture $AP_2$ is provided to select the correct order of the diffraction mode of the acousto-optic modulator $AOM_2$. The object beam is deflected downward by the beam splitter $BS_2$ and focused on the object by the lens $L_1$. Light reflected from the object goes through the beam splitter $BS_3$ and is reflected on the detector DET. Part of the object beam goes through the beam splitter $BS_3$ and is imaged by the eyepiece$_1$. Eyepiece$_1$ and doublet lens $L_1$ form a low power microscope for visualizing the object.

The reference beam is frequency shifted (44 mHz) by the acousto-optic modulator $AOM_1$. It is reflected by mirrors $M_3$, $M_4$ and beam splitters $BS_2$ and $BS_3$ to fall on the detector DET and overlap with the object beam. The eyepiece$_2$, mirror M$_5$ and lens L$_2$ are provided to view the detector face through the beam splitter BS$_3$. This allows orientation and adjustment of the reference and object beams at the detector so that the interference pattern has a minimum number of fringes. The detector output at 1 mHz is shifted in frequency to 89 mHz using the balanced mixed and the 88 mHz local oscillator so that it can be demodulated by the FM tuner.

Figure 11:
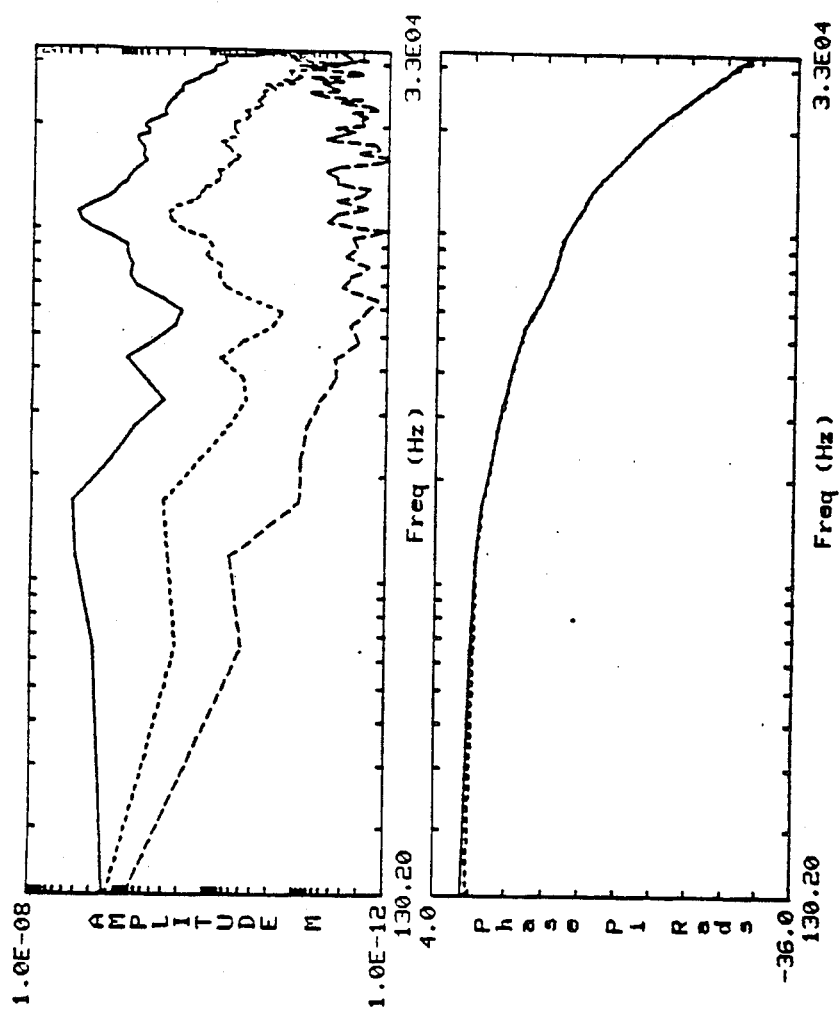

FIG. 11. Amplitude (top) and phase (bottom) of round window vibration as a function of frequency. Vibration amplitude was determined at 60 dB SPL (solid line), 40 dB SPL (dotted line) and with sound turned off (dashed line). Phase was measured at 60 dB SPL (solid line) and at 40 dB SPL (dotted line). The noise level (N) is frequency dependent. It is highest at low frequencies (130 Hz) and decreases with increasing frequency up to a frequency of 6 kHz at a rate of approximately $-10$ dB per octave. The noise remains essentially flat up to a frequency of 20 kHz and then increases in magnitude up to 33 kHz. The round window vibration amplitude at 60 dB SPL is $1.5 \times 10^{-8}$ meters between 1 and 2 kHz. The response shows minimums near 3 kHz and 6 kHz and a peak near 20 kHz. The response decreases between 20 and 33 kHz. S/N ratio is adequate ($>20$ dB) at all frequencies between 300 Hz and 30 kHz. At 40 dB SPL the S/N ratio is adequate only at a few selected frequencies.

Figure 12:
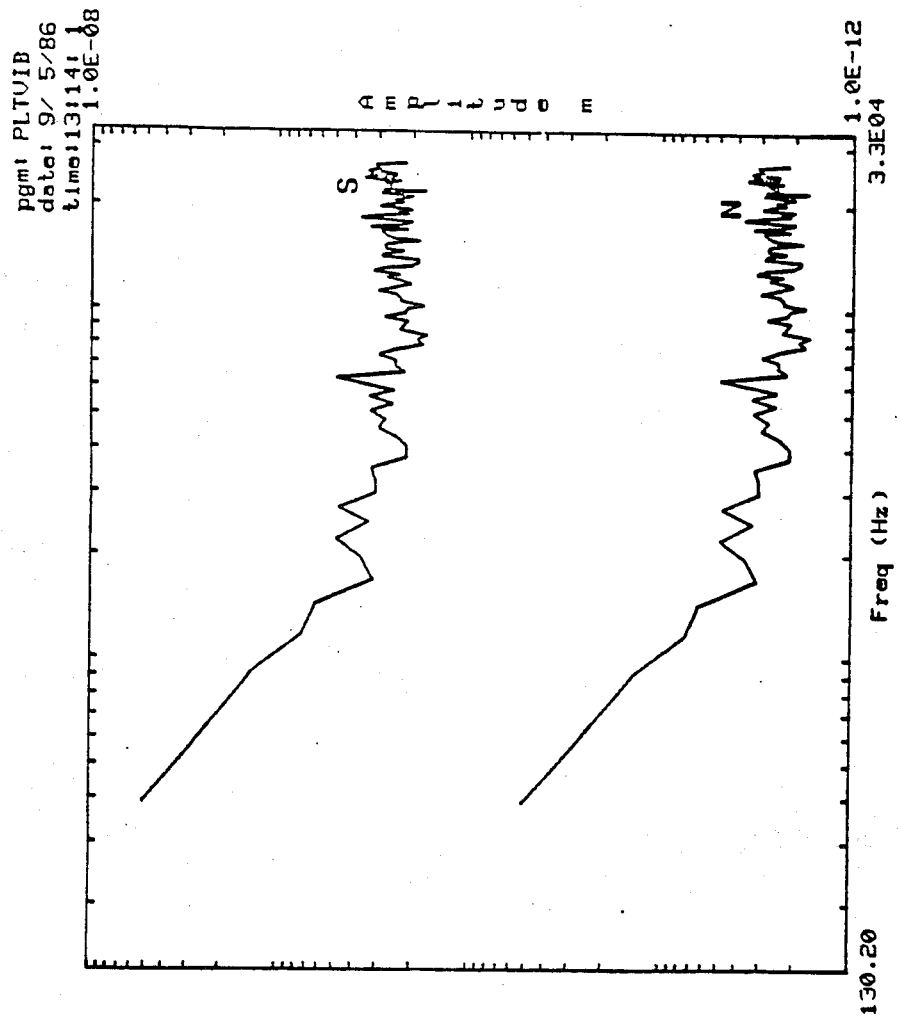

FIG. 12. Round window vibration amplitude (S) and noise (N) measured as a function of frequency. Note that noise level has been averaged over ten frequencies around each measuring frequency. The noise level shows a frequency dependence similar to that illustrated in the previous figure except that the shape of the curve is slightly different due to averaging. Round window vibration amplitude was measured for a 40 dB S/N ratio. The amplitude varied from $5 \times 10^{-9}$ m at 0.4 kHz to about $3 \times 10^{-10}$ meters at frequencies between 10 and 30 kHz.

Figure 13:
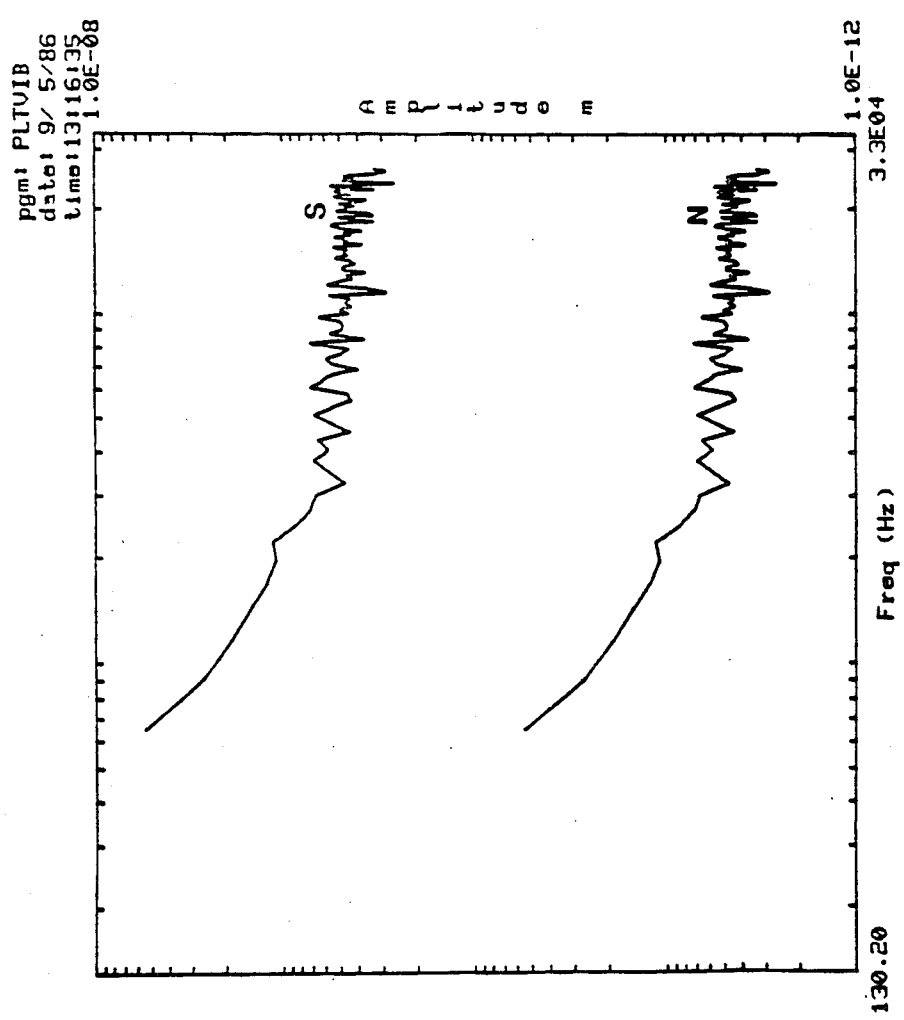

FIG. 13. Round window vibration amplitude (S) and noise (N) measured as a function of frequency. Measurements were made at the same spot used for measurements in FIG. 12 after readjustment of the interferometer, and as a consequence the noise floor is slightly higher.

Figure 14:
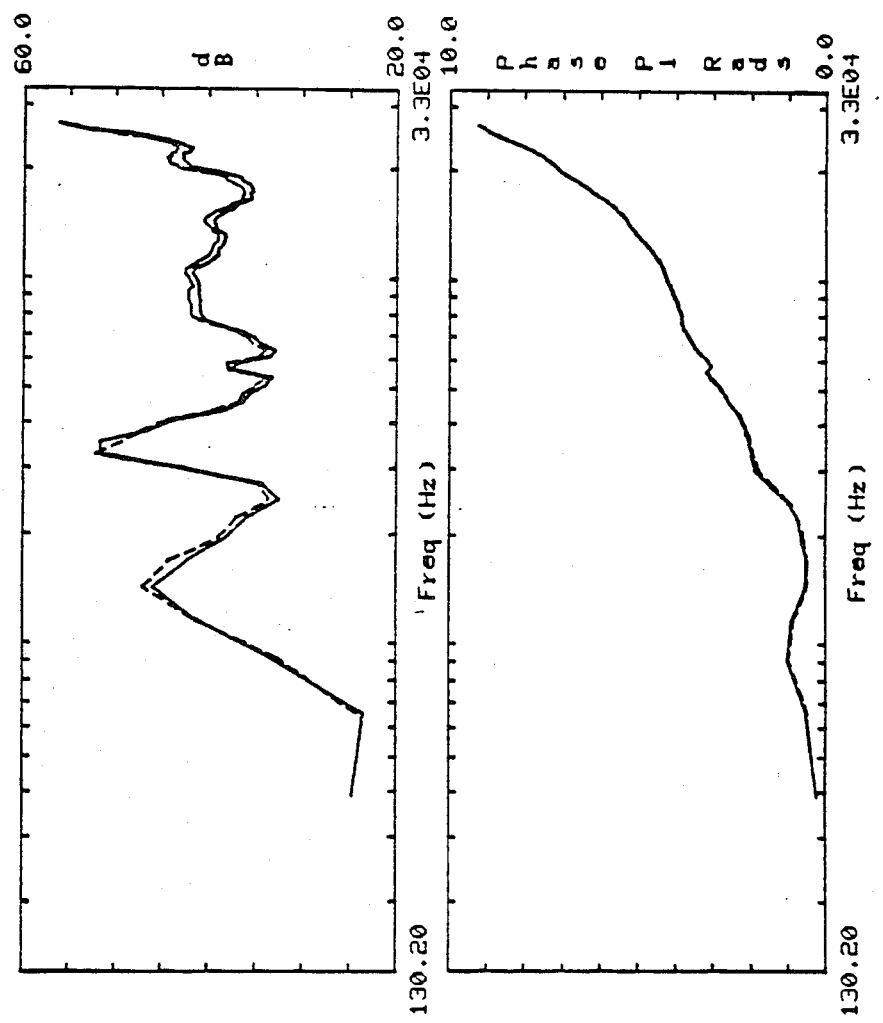

FIG. 14. Sound pressure level required to produce $10^{-10}$ m round window vibration amplitude as a function of frequency (top) and vibration phase as a function of frequency (bottom). The two amplitude curves have been calculated from the data shown in FIGS. 12 and 13. The close agreement between the two sets of data (solid line and dashed line) shows excellent repeatability. Similar close agreement is shown for the phase data (bottom curves).

Figure 15:
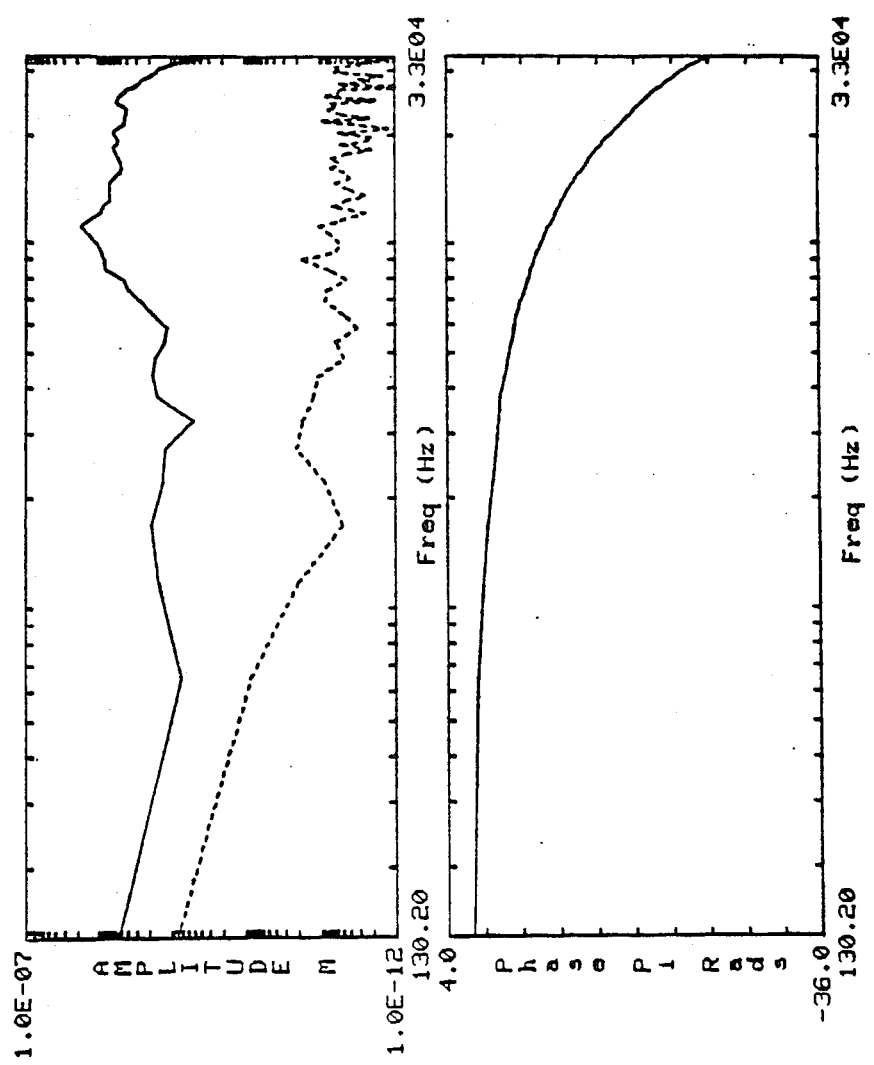

FIG. 15. Amplitude (top) and phase (bottom) of basilar membrane vibration as a function of frequency. Vibration amplitude and phase was determined for 60 dB SPL (solid line) and nose with sound turned off (dashed lines). The noise level varies with frequency in a manner similar to that shown for the round window membrane in FIG. 11. The S/N ratio is about 17 dB at frequencies below 0.7 kHz and much higher (up to 66 dB) at frequencies between 0.7 kHz and 33 kHz.

DETAILED DESCRIPTION OF THE INVENTION

This invention concerns a heterodyne interferometer for measuring the amplitude of vibration of a vibrating object. The interferometer comprises:
 (a) a laser for emitting a monochromatic light wave;
 (b) a beam splitter for splitting the light wave into an object light wave and a reference light wave, each having the same frequency;
 (c) a modulator for changing the frequency of the object light wave and the reference light wave so as to produce a predetermined offset between the frequency of the object light wave and the frequency of the reference light wave, said modulator being so positioned with respect to the beam splitter that the object light wave and the reference light wave pass through the modulator thereby changing their frequencies;
 (d) means for directing the object light wave onto the vibrating object, said means so positioned between the object and the modulator that at least a portion of the object light wave is directed onto and reflected off of the object;
 (e) a photodetector for producing, at a frequency equal to the predetermined offset, a beat signal varying in accordance with variations in the interference resulting from combining at least a portion of the reflected object light wave and the reference light wave, the photodetector being so positioned with respect to the object and the beam splitter that it detects and measures the interference; and
 (f) means for processing the beat signal to measure variations in its phase or amplitude, said means being electrically connected to the photodetector in order to receive the beat signal.

Essentially any modulator for changing the frequency of a light wave may be used in the practice of the subject invention. Presently, the preferred modulator is an acousto-optical modulator. In the preferred embodiment of the invention, one acousto-optical modulator is employed on the reference light wave and a second acousto-optical modulator is on the object light wave. The acousto-optical modulators are driven by predetermined frequencies which differ by the predetermined offset.

The means for directing the object light wave onto the object whose vibration is to be measured may comprise a variety of optical devices. Suitable devices are those which are capable of directing a light wave, such as mirrors, lens, combinations of lens (e.g. a microscope), etc. In the preferred embodiment, the means for directing the object light wave comprises a microscope or a part thereof, i.e. the objective lens.

Suitable photodetectors are those which do not suffer a loss of sensitivity when the level of light reaching the photodetector is low. Merely by way of example suitable detectors include a photomultiplier tube, a photoconductive device, and a PN Junction device. Since PN junction devices, such as a reverse-biased silicon PN photodiode, are small, rugged, and readily available at low cost, they are presently the preferred photodetectors for use in the heterodyne detection system of the subject invention.

There are a number of variations in the configuration of useful PN junction photodiodes: the abrupt or graded junction, the PIN structure, and the avalanche device. In the PIN structure, an intrinsic, high-resistivity layer is sandwiched between the P and N regions; hence the acronym PIN. It is constructed so that the potential drop occurs mainly across the intrinsic layer. This layer is sufficiently long to insure that most of the incident photons are absorbed within it, thereby minimizing the travel distance for the carriers and maximizing the charge flow in the external circuit (responsivity). By increasing the reverse bias across a PN junction, the field in the depletion layer can increase to a point where the carriers eject new electrons from the valance to the conduction band, while still traversing the layer. The result is a multiplication effect (avalanche) of the current, which creates gain in the manner that a photomultiplier tube does. The gain (M) can reach a factor of several hundred.

Unfortunately, carrier avalanche gain is not quite as noise-free as that provided by the photomultiplier secondary-emission process, principally because of the contribution of two kinds of carriers (electrons and holes) to the multiplication process. The avalanche device is, nevertheless, particularly useful in direct (video) detection where the gain provides an increase in the SNR by enhancing the shot noise contribution (along with the signal) while the thermal (amplifier) noise remains constant. By optimally adjusting the gain, the minimal detectable power is improved over the ordinary photodiode by a factor that is approximately equal to the gain.

In the heterodyne configuration, however, it has already been pointed out that optimal detection is available with the reverse-biased PN junction photodiode without avalanche multiplication, when the local oscillator (LO) signal is sufficiently strong and the beams are aligned parallel to each other. In this case, the avalanche gain provides a stronger signal (by a factor of $M^2$), but it also provides an even stronger shot noise (by a factor of $Mn$ where $2 < n < 3$). Thus it is contemplated that the avalanche device will be useful in the heterodyne mode only when there is insufficient LO power to swamp the thermal (amplifier) noise.

The means for processing the beat signal may utilize phase-demodulation or frequency-demodulation techniques. Presently the preferred approach is to use a standard FM-demodulator. Such demodulators are readily available in the form of FM-receivers.

The invention also provides a method for measuring the amplitude of vibration of a vibrating object. In one embodiment, the method comprises using the heterodyne interferometer of this invention. In another embodiment, the method comprises:

(a) generating a monochromatic light wave;
(b) splitting the light wave into an object light wave and a reference light wave;
(c) changing the frequencies of the object light wave and the reference light wave by passing the object light wave and the reference light wave through a modulator to produce a predetermined offset between the frequencies of the object light wave and the reference light wave;
(e) combining at least a portion of the reflected object light wave and the reference light wave to form an interference;
(f) measuring the interference in such a manner so as to produce a beat signal at a frequency equal to the predetermined offset having variations corresponding to variations in the interference; and
(g) processing the beat signal so as to measure variations in its phase or amplitude.

Essentially the amplitudes of vibrations of any vibrating object may be measured by the method of this invention. This invention is particularly useful when the amplitudes of vibration are submicroscopic in magnitude, i.e. below about $10^{-7}$ cm, or when the vibrating object has low reflectivity, i.e. below about 0.02%. Presently, it is contemplated that the subject inventions will be used to measure the vibration of biological tissues, such as the vibrations of structures of the inner ear or of the eye. In one embodiment of the invention, the vibrations of the basilar membrane is measured. In another embodiment, the vibrations of the hair cells of the organ of Corti are measured. Certain embodiments of this invention are exemplified in the Examples and Experimental Discussion which follow. The Examples and Experimental Discussion are set forth to aid in an understanding of the invention but are not intended to, and should not be construed to, limit in any way the invention as set forth in the claims which follow thereafter.

Experimental Discussion

The heterodyne laser interferometer described herein was specifically designed for vibration measurement of biological tissue. One application is for the study of the vibration of individual cellular elements of the organ of Corti. In order to successfully measure vibration of single cellular elements, the interferometer had to designed to work under unique conditions:

(i) The size of the surfaces whose vibration is to be measured is small (A hair cell diameter is between 5 and 15 $\mu$m [27-31]; the surface is also not flat);

(ii) The reflectivity of the cells is very low, as they are nearly transparent;

(iii) The vibration amplitudes to be measured are very low (The mechanical response of the cochlea is nonlinear even at modest levels of sound pressure; therefore, in order to measure responses at threshold sound pressure levels, the vibration sensitivity of the interferometer has to be at least $10^{-11}$ meters [18,9-14]);

(iv) The frequency response of the interferometer has to be wide (In the basal region of the cat cochlea accessible through the round window opening, characteristic frequencies are expected to be in the region of 35 kHz [33]; accordingly, to observe the complete response, the frequency response of the interferometer should extend to at least 50 kHz);

(v) The mechanical characteristics of the inner ear structures are nonlinear [12,13,34], therefore, the linearity of the interferometer must be high;

(vi) The sensitive vibration measurements are to be made on living animals (Low frequency noise due to breathing, blood circulation of the animal and muscle movements will be superimposed on the vibrations to be measured); and (vii) The incident light level should be kept below 0.5 watts/cm$^2$ since there is evidence that high intensity of incident light may damage the cochlear cells.

Figure 1:
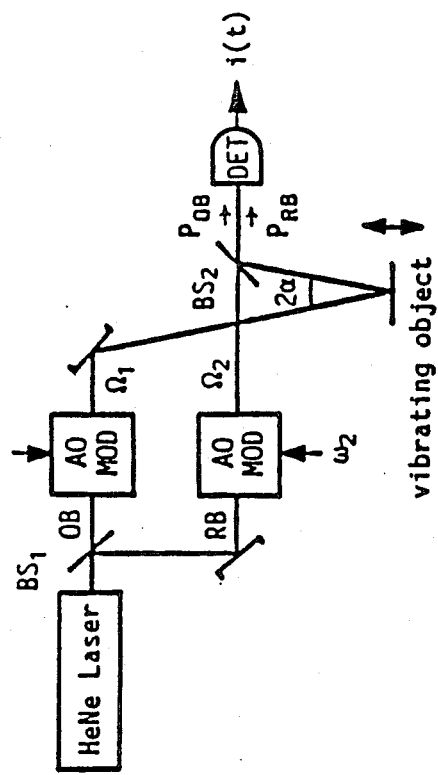
FIG. 1. Basic elements for heterodyne interferometry. After separation by a beam-splitter, the object beam (OB) and the reference beam (RB) are shifted in frequency by two acousto-optical modulators (AO MOD). The object beam frequency is $\Omega_1$ and the reference beam frequency is $\Omega_2$. After reflection on the vibrating object, the object beam is combined with the reference beam at the second beam-splitter producing a beat signal $(\Omega_1-\Omega_2)$ which is detected by a photodetector (DET). $P_{OB}$ and $P_{RB}$ are the light powers of the object and reference beam, respectively, received by the detector (DET).

The principle of heterodyne interferometry is very simple in concept. It is illustrated in FIG. 1. The basic idea is to introduce (by means of two acousto-optical modulators) a small frequency shift $\Delta\omega$ between the optical frequencies and $\omega_1$ and $\omega_2$ of the two interfering beams. Due to this frequency difference ($\Delta\omega = \Omega_1 - \Omega_2$), the interference between the reference beam (RB) and the object beam (OB) reflected from the vibrating object produces an intensity modulation of the light field at the beat frequency $\Delta\omega$. This intensity modulation is detected by a photodetector (DET). Displacement of the object changes the optical path length and therefore the phase of the object beam. This is converted directly into a change of phase of the beat frequency. As long as $\Delta\omega$ is chosen small enough to be resolved by the photodetector, the photocurrent is given by $$i(t) = a + b \cos[\Delta\omega t + \Phi(t)], \quad (1)$$

where a is the dc and b the ac amplitude of the photocurrent and $\Phi(t)$ is the phase difference between the two interfering beams. The information about the object movement is contained in the phase $\Phi(t)$ of the beat frequency $\Delta\omega$. This phase can be measured electronically. An advantage of the heterodyne system is that the phase angle is not affected by intensity fluctuations of the interfering beams.

In case of vibration analysis, the interference phase in Eq.(1) is a periodic function of the form $$\Phi(t) = \beta u \cos(\Omega t + \psi) + \Phi, \quad (2)$$

where u is the amplitude, $\Omega$ the frequency, $\psi$ the phase of the vibration, $\Phi$ is a constant phase, and $\beta$ is a geometrical factor. If 2 $\alpha$ represents the mutual angle between the illumination and observation directions (see FIG. 1) and the $\lambda$ wavelength or the laser, $\beta$ is given by $$\beta = (4\pi/\lambda) \cos \alpha. \quad (3)$$

Combination of Eqs. (1) and (2) shows that the detector output is a phase or a frequency-modulated signal with carrier frequency $\Delta\omega$ and modulation frequency $\Omega$. The corresponding spectrum of such a signal is a discrete Bessel spectrum, centered at $\Delta\omega$. For small vibration amplitudes, this spectrum consists essentially of three lines: the carrier and the first upper and lower sidebands. Thus, small vibrations amplitudes are readily found from the power ratio of the carrier ($P_0$) and the first sideband ($P_1$) by the relation $$(P_0/P_1)^{\frac{1}{2}} = J_0(\beta u) \approx 2/(\beta u) \quad (4)$$

where $J_0$ and $J_1$ are Bessel functions of integer order [37]. The power $P_0$ and $P_1$ can be measured with a spectrum analyser.

Carrier-to-noise ratio in heterodyne detection:

The sensitivity is essentially determined by the carrier-to-noise ratio (CNR), or in other words, by the power ratio of the beat signal and the noise after detection. To estimate the CNR value, two noise sources have to be considered: first, the shot-noise which is due to the quantum nature of the light, and second, the thermal-noise (or Johnson-noise) of the electronics. The electrical power of the thermal-noise at the output of the detector amplifier, which is used as current-to-voltage converter, is given by [38]

$$P_{TN} = 4 kT B R_0/R, \quad (5)$$

where $k = 1.38 \cdot 10^{-23}$ J/K is the Boltzmannn constant, T the absolute temperature, $R_0$ the feedback resistance, R the load resistance, and B the bandwidth. Equation (5) shows that the thermal-noise is independent of the detected optical power, in contrast to the shot-noise, which is known to be essentially determined by the average light power ($P_0$) (falling on the detector [38]. The electrical power corresponding to the shot-noise at the output of the detector amplifier is given by $$P_{SN} = 2(R_0^2/R) e B S \overline{P_0}, \quad (6)$$

where e is the electron charge and $S = \eta e/h\nu$ is the spectral sensitivity of the photodetector. It is determined by the quantum efficiency $\eta$, the electron charge e and the photon energy $h\nu$. It the detector aperture is sufficiently large in comparison with the beams sizes, $\overline{P_0}$ is the sum of the light powers in the reference ($P_{RB}$) and object ($P_{OB}$) beams, both measured after the beamsplitter $BS_2$ shown in FIG. 1, ($\overline{P_0} = P_{RB} P_{OB}$).

On the other hand, the electrical power or the heterodyne signal is given by $$P_{ac} = 2(R_0^2/R) m^2 S^2 P_{OB} P_{RB}, \quad (7)$$

where m represents the relative interference amplitude. This factor is maximum and equal to 1 when the interference is maximum, i.e. when the two interfering beams are well superimposed. From Eqs. (6) and (7), it is now possible to find the carrier-to-noise ratio CNR for shot-noise-limited detection, namely $$CNR = P_{ac}/P_{SN} = (\eta/h\nu)(m^2/B) [P_{OB} P_{RB}/(P_{OB} + P_{RB}]. \quad (8)$$

Assuming that m = 1 (maximum interference) and $P_{RB}$ is much greater than $P_{OB}$, this equation becomes $$CNR = (\eta P_{OB}/h\nu)/B. \quad (9)$$

Equations (6) and (7) show that both the electrical power of the shot-noise $P_{SN}$ and the electrical power of the signal $P_{ac}$ increase with increasing optical power $P_{RB}$ of the reference beam. However, Eq.(9) indicates that the shot-noise-limited CNR becomes independent of the reference beam power $P_{RB}$ if $P_{RB}$ dominates the object beam power $P_{OB}$. In fact, Eq. (9) corresponds to the maximum CNR value that can be obtained with a given light power in the object beam. In order to attain this most favorable situation of shot-noise-limited detection, one has to make sure that the shot-noise (Eq.(6)) dominates the thermal-noise of the electronics (Eq. (5)). This is always possible by sufficiently increasing the reference power $P_{RB}$ (which is supposed to be free of excess noise). The resulting improvement of the CNR is known as "heterodyne gain".

Shot-noise-limited sensitivity:

Since the incident light power of the living cells must be kept below 0.5 W/cm² and since the reflectivity of these cells is very low (less than $2.10^{-4}$), the power in the object beam $P_{OB}$ is very low too. Thanks to the heterodyne gain described above, one can overcome the thermal noise of the detection system even for a photodiode (see Eqs. (5), (6), (7) and (8)). Therefore, one is not constraint to use a photomultiplier which has inherent low noise amplification but poor quantum efficiency. A silicon photodiode will provide a considerably better CNR value than a photomultiplier, because the quantum efficiency of photodiodes is typically 80%, whereas it is only between 5% to 10% for photomultipliers.

An important quantity is the minimum reference power $P_{RB}$ for which the detection begins to be shot-noise-limited. Using Eqs. (5) and (6) and assuming that $P_{RB}$ is greater than $P_{OB}$, one gets $$P_{RB,min} = 2 kT/(eR_0 S). \quad (10)$$

For example, with a feedback resistance R=56 k α, and a temperature T300° K., this limit is found to be $P_{RB,min}=2.3$ μW. As a consequence, the reference power must be greater than this value to be sure that the detection is really shot-noise-limited. Practically, one can test in a simple manner whether the shot-noise is the dominant noise contribution or not, by blocking the light in detector amplifier. If the noise level goes down when blocking the light, the detection is shot-noise-limited and has maximum CNR.

Finally, using Eq.(4), one finds for the minimum detectable vibration amplitude $$u_{min} = 2/(\beta \sqrt{CNR}). \qquad (11)$$

For example, with a quantum efficiency $\eta=77\%$, a photon energy $h\nu=3.1\cdot10^{19}$ Ws ($\lambda=633$ nm) and $P_{OB}=50$ nW, the shot-noise-limited CNR for 1 Hz bandwidth is equal to 111 dB, or 76 dB for 3 kHz bandwidth. For normal incidence ($\alpha=0°$, $\beta=19.9$ μm$^{-1}$), the corresponding minimum detectable amplitude, or in other words, the noise equivalent vibration amplitude is then equal to $u_{min}=0.28\cdot10^{-12}$ m (for 1 Hz bandwidth).

Effects of the optical properties of the structure under study:

It was assumed so far that the surface of the objects under study was optically flat. For a given incident light power, it is evident that the curvature and the roughness of the vibrating surface have a strong influence on the CNR. In case of specular reflection on distorted surfaces for example, the optical power which is relevant for the CNR if given by the power of the back-reflected portion of light which corresponds to the same optical mode as the reference. The power of this portion can be considerably smaller than the total power of the reflected beam. In the extreme case of diffusely scattering surfaces, the reflected beam shows speckles. Since the interference within each speckle is statistically independent of the others, the contributions from all speckles add up only incoherently. Therefore, $P_{OB}$ in Eqs.(8) and (9) for the CNR has to be replaced by the optical power within one speckle, i.e. within one correlated cell of the back-scattered light 37,39].

Signal processing:

The final step of heterodyne detection consists in the extraction of Φ(t) from a signal of the form given by Eq. (1). Two different methods can be used, namely phase- or frequency-demodulation techniques. The simplest approach is to use a standard FM-discriminator. FM-demodulation of the detector output would produce a signal which is proportional to the instantaneous velocity of the mechanical movement versus time, as it is well known from laser Doppler velocimetry [40]. For vibration frequencies between 10 Hz and 100 kHz, such demodulators are readily available for carrier frequencies in the range of 87 MHz to 108 MHz in the form of standard FM-receivers. From the beat frequency, which has to be adapted to the detector response, a suitable carrier frequency is easily obtained by frequency translation using a mixer and local-oscillator (see FIG. 2).

FM-demodulation has several advantages: first, FM-receivers are readily available; second, no external reference oscillator is needed for the demodulation; finally, FM-demodulation allows high phase excursions at low frequencies, which is particularly important when measuring vibrations in living animals. On the other hand, FM-demodulators displacement sensitivity decreases with frequency. The most serious drawback is the well known "threshold effect" which characterizes FM-demodulators [41]. When the carrier-to-noise ratio equals about 10 dB for the full receiver bandwidth (typically 150 kHz), the signal-to-noise ratio at the demodulator output shows a rapid deterioration. This threshold (which corresponds to 27 dB for 3kHz bandwidth) determines the minimum CNR for which the FM-demodulator works properly. Nevertheless, a conventional FM-receiver is a powerful demodulation system for heterodyne detection.

EXAMPLE 1

Figure 2:
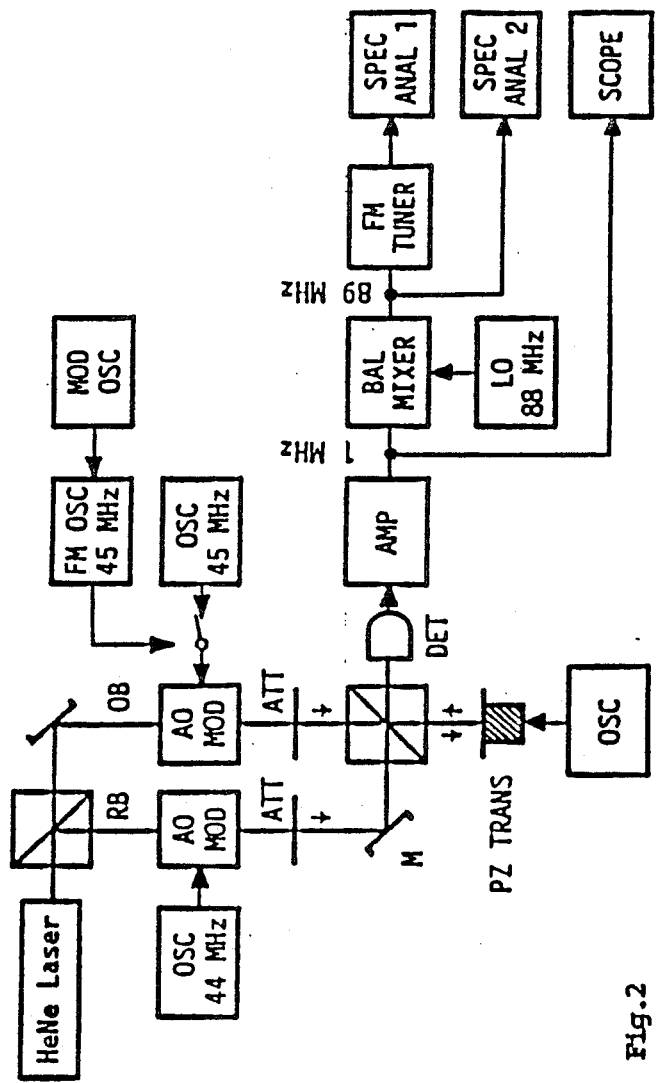
FIG. 2. Experimental arrangement for testing the performance of interferometer. The system consists of (1) and HeNe-laser, (2) equipment to generate the necessary frequency offset for heterodyne detection, viz. acousto-optical modulators (AO MOD) and driving oscillators (OSC), (3) a photodetector (DET) and the associated amplifier (AMP), (4) equipment to translate the carrier frequency, viz, a balanced mixer (BAL MIXER) and a local oscillator (LO), (5) equipment to control, demodulate and measure the interference signal, viz. an oscilloscope (SCOPE), a RF-spectrum analyzer (SPEC ANAL 2, HP 8553B), a FM-tuner (FM-TUNER, Revox B760) and a LF-spectrum analyzer (SPEC ANAL 1, HP 3582A), and finally (6) equipment to generate an artificial FM-signal (FM OSC, MOD OSC) for the calibration of the FM-demodulator. The mirror mounted on a PZ-translator is used as the vibrating object.

Method:

The experimental arrangement used to determine the performance of the heterodyne interferometer is shown schematically in FIG. 2. The most common method to produce the necessary frequency offset for heterodyne detection consists in using two acousto-optical modulators (one in each beam, see FIG. 1) driven at $\omega_1$ and $\omega_2$, respectively. Several diffracted beams are produced by these modulators. The first order beams (which are selected by an appropriate mask) are shifted in frequency, due to the Doppler effect, by either $+\omega_{1,2}$ or $-107_{1,2}$, depending on whether the diffraction is in the direction of the travelling acoustic wave or opposite to it. The net frequency shift between the two interfering beams is then given by $\Delta w = w_1 \pm w_2$. The operation bandwidth of such modulators is typically 10 MHz and centered at 40 MHz. The diffraction angle is typically 5 mrad, which is about 15 times the diffraction limited divergence of a 1 mm diameter laser beam. In order to get maximum optical power in the diffracted beams (i.e. about 90% of incident light power), the angular position of the modulators have to be adjusted properly, to fulfill the Bragg condition. By using two modulators instead of a single one, the heterodyne frequency can be chosen in a wide range of frequencies. Furthermore, the unavoidable electromagnetic pick-up by the detector from the modulators (driven with 2 watts RF-power) has no disturbing effects on the interference signal in this case, because perturbations due to EM coupling are separated from the signal in frequency. Actually, the acousto-optical modulators are driven with 44 MHz and 45 MHz, respectively, so that the net frequency shift between the object beam (OB) and the reference beam (RB) is equal to 1 MHz. This frequency difference was selected so that it was within the flat part of the detector response. It is translated into the frequency range of the FM-receiver with the help of a balanced mixer and a local oscillator at 88MHz, yielding a carrier frequency of 89 MHz. Two optical attenuators (consisting of variable neutral density filters) allow independent adjustment of the optical power of the object and reference beam. Finally, a mirror mounted on a vibrating PZ-translator is used as the vibrating object.

As shown in FIG. 2, three instruments are used for measurement and test purposes: an oscilloscope (SCOPE) to monitor the interference signal, a RF-spectrum analyzer (SPEC ANAL 2) for measuring CNR before demodulation and for calibration, and LF-spectrum analyzer (SPEC ANAL 1) for the vibration analysis after demodulation. The oscilloscope is used to adjust the superposition of the two interfering beams by maximizing the beat signal. Note that the modulation depth of the interference is given by $2m^2P_{OB}P_{RB}/$ ($P_{OB}+P_{RB}$), where m is the relative interference amplitude. The FM-receiver used for demodulation is a commercially available Revox B760 tuner. It uses a demodulation principle known as "coincidence demodulation". This principle is based on a delay line which converts frequency deviations into phase deviations. Phase deviations are then detected by means of a balanced mixer followed by a low-pass filter. Exact calibration of the FM-demodulator versus frequency can be obtained from carrier cancellation occuring when $J_o=0$ for a sinusoidal modulation, observed with a RF-spectrum analyzer (SPEC ANAL 2 in FIG. 2), and by measuring the corresponding voltage at the demodulator output. For this purpose, one of the two acousto-optical modulators can be driven with a frequency-modulated oscillator (FM OSC 45 MHz in FIG. 2). Note that this FM-oscillator can also be used for vibration simulations in order to test the complete system.

Figure 3:
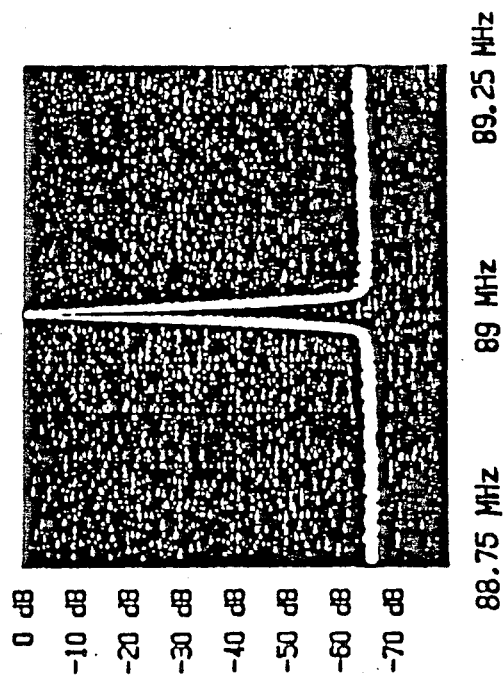
FIG. 3. Spectrum of the carrier frequency (beat signal) at the output of the mixer. This spectrum was measured for an incident light power of 0.5 mW and a simulated reflectivity of the object surface of 0.002%

Results:

In order to compare experimental results with theoretical predictions, CNR measurements for an incident light power of 0.5 mW and three different values of specular reflectivity (0.2%, 0.02%, and 0.002%) have been made (FIG. 3 and Table 1). The calculated value of CNR was 76 dB for 3kHz bandwidth and 50 nW object beam power. It is in good agreement with the measured value of 75 dB (Table 1). For these measurements, the change of the reflectivity was simulated with the attenuator located in the object beam. Furthermore, the reference power was chosen sufficiently large ($P_{RB}=100$ μW) compared with the limit given by Eq. (10), to make sure that the CNR was really shot-noise-limited.

TABLE 1

Shot-noise limited CNR measured for a given incident light power (0.5 mW) and three different values of specular reflectivity.

| Reflectivity | Measured $P_{OB}$ | Measured CNR (for 3 kHz bandwidth) |
| --- | --- | --- |
| 0.002% | 5.2 nW | 65 dB (see FIG. 3) |
| 0.02% | 52 nW | 75 dB |
| 0.2% | 520 nW | 85 dB |

Noise characteristics:

Measurements were made at three different vibration frequencies, viz. 500 Hz, 5 kHz, and 25 kHz. The noise level at the demodulator output is shown as a function of CNR in FIGS. 4.1, 4.2, and 4.3, respectively. Each of the curves in FIGS. 4.1, 4.2 and 4.3 can be divided into four distinct parts: A, B, C and D. In order to understand these curves, one has to distinguish two different noise contributions: first, the internal tuner noise (ITN), and second, the applied input noise (AIN). The first one is generated by the tuner itself and has a fixed level, whereas the second one has a level which varies with the CNR at the tuner input. In part A, i.e. for large CNR values, the output noise level is independent of CNR, since ITN predominates. In part B, the noise is essentially due to AIN. Therefore the output noise decreases linearly as CNR increases. In part C, the noise increases very steeply. This is due to the FM threshold effect described above. Note that the breakpoint between part B and C corresponds approximately to the predicted CNR value of 27 dB for 3 kHz BW. In part D, i.e. for low carrier level (CNR is less than 15 dB for 3 kHz BW), the noise again remains constant, because in the absence of the carrier the receiver gain is set to maximum (the automatic gain control is saturated and therefore the level of the output noise is increased). Comparison of part A in the FIGS. 4.1, 4.2, and 4.3 indicates that the ITN component (which is predominant in this part) has the same level (−119 dBV) at 25 kHz and 5 kHz but is slightly higher (−109 dBV) at 500 Hz. Additional measurements of the output noise spectrum indicate that the level of the ITN is approximately flat above 1 kHz, but rises at low frequencies. Comparison of part B in the three figures shows that the noise level is frequency dependent for a given CNR, due to the fact that a white phase noise at the demodulator input appears triangular at the output. In this region, the noise increases by 20 dB for each decade increase in frequency. Finally, the noise level in region D, as well as the break-point between part B and C, are frequency independent. It should be pointed out that useful measurements with an FM-demodulator can only be made for CNR values in excess of 30 dB (for 3 kHz bandwidth).

Figure 5:
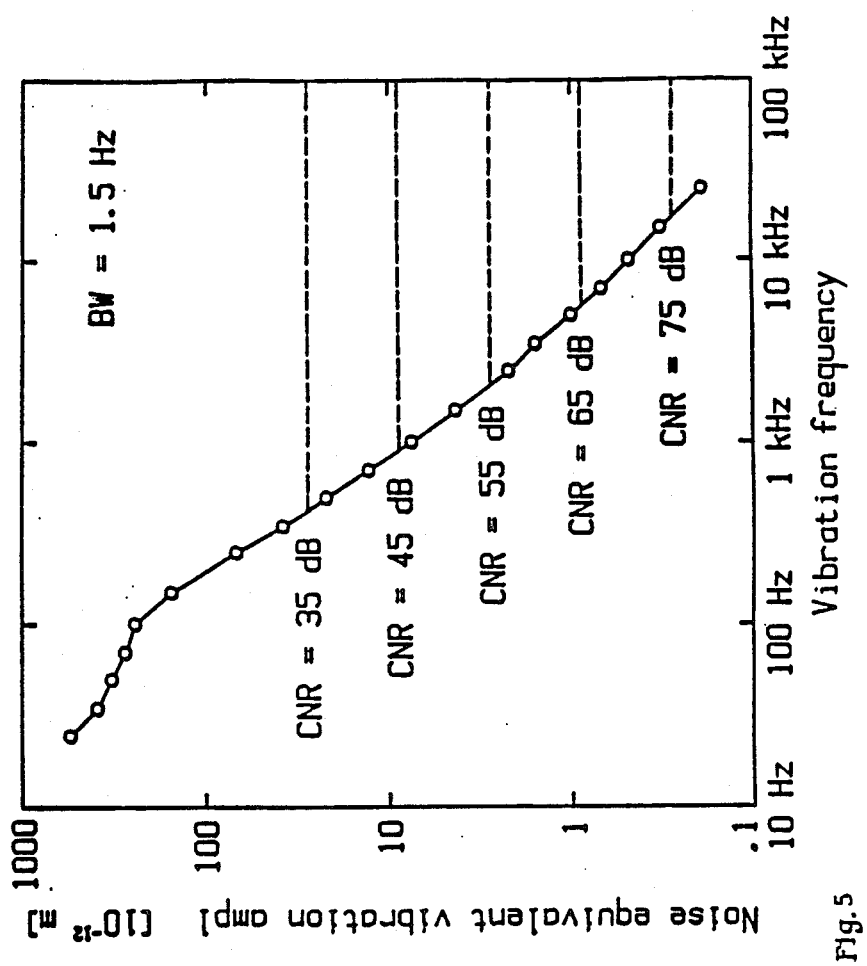
FIG. 5. Noise equivalent vibration amplitude versus frequency, for a 1.5 Hz detection bandwidth. The CNR values were measured in 3 kHz bandwidth. The curves show the lowest vibration amplitude that can be detected (S=N) by the heterodyne system. At high frequencies, the sensitivity is essentially limited by the CNR (horizontal dashed lines), independently of frequency. At low frequencies, the sensitivity decreases at roughly 20 dB per decade.

FIG. 5 shows the noise equivalent vibration amplitude, or in other words, the minimum detectable vibration amplitude, as a function of vibration frequency. This noise equivalent vibration amplitude is given for 1.5 Hz detection bandwidth and different values of CNR (as parameter). At high frequencies, the noise equivalent vibration amplitude is essentially limited by the CNR (horizontal dashed lines), independently of frequency, and at lower frequencies by the demodulator noise characteristic (ITN, solid line). The demodulator noise characteristic (solid line) was determined experimentally by using a unmodulated carrier with 86 dB CNR (3 kHz BW). The minimum detectable vibration amplitude corresponding to this noise level was then calculated by $$u_N = V_N/(\beta\, S_{FM}f), \qquad (12)$$

where $V_N$ represents the noise level (in volts) at the demodulator output, $S_{FM}$ the sensitivity of the FM-demodulator ($S_{FM}=16.5$ mV/kHz in our case) and f the vibration frequency. For CNR values higher than 85 dB (3 kHz BW), one can see that the sensitivity depends only on the tuner noise characteristics over the entire frequency range.

Figure 6:
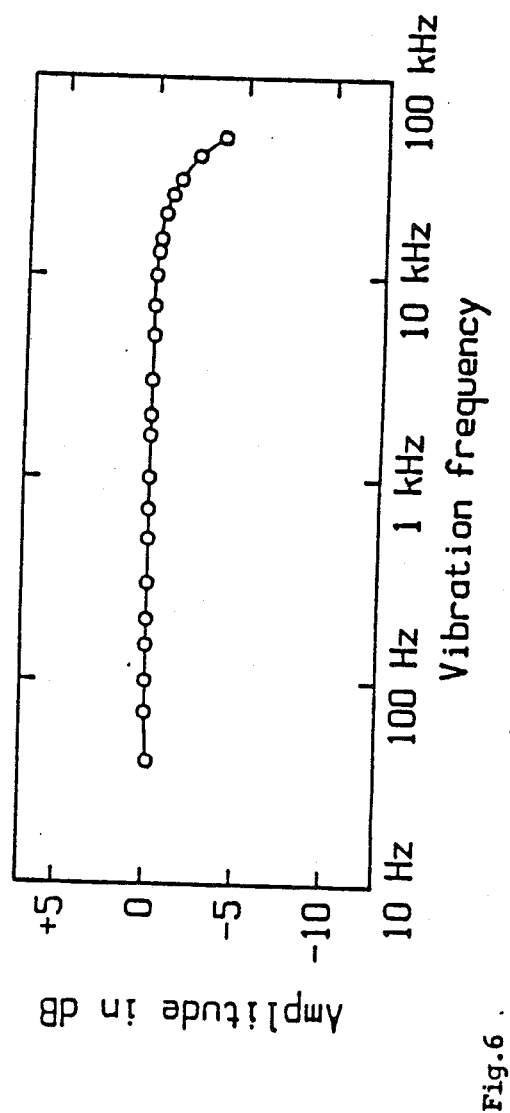
FIG. 6. Amplitude response of the interferometer for a fixed vibration velocity, i.e. for a fixed frequency excursion. The amplitude response is extremely flat, and the 3 dB bandwidth is about 45 kHz.
Figure 7:
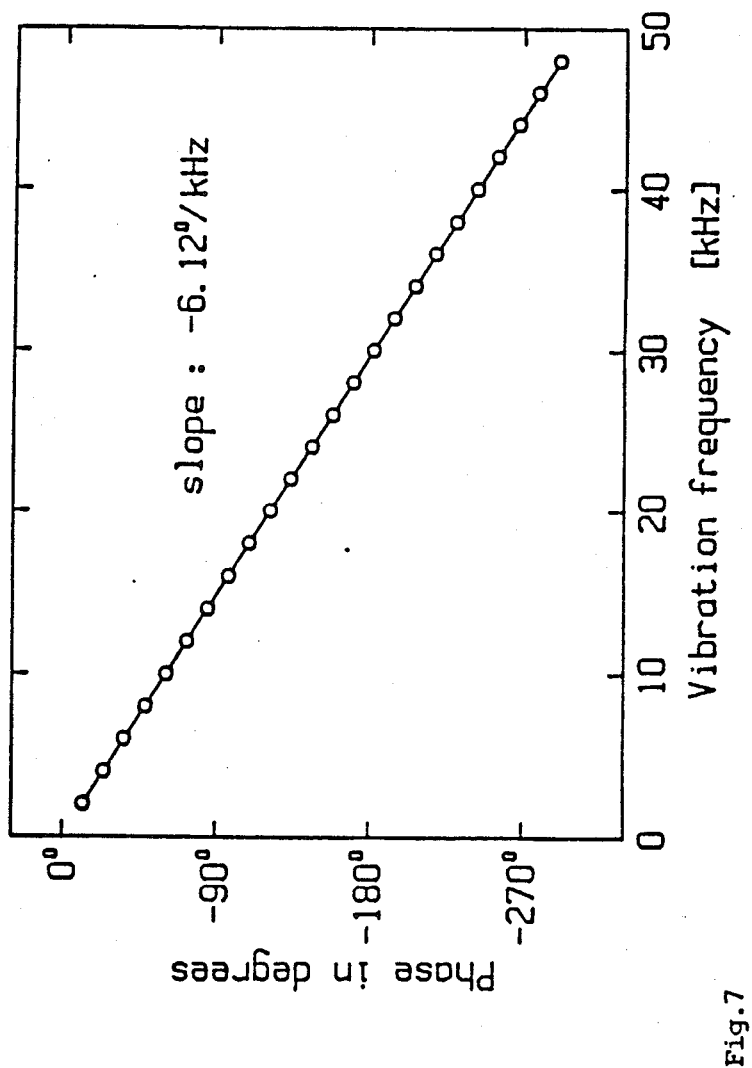
FIG. 7. Phase response of the interferometer. The phase changes linearly with the frequency. The phase lag of $-6.12°/kHz$ corresponds to a delay of 17.0 $\mu$s.

Amplitude and phase response:

FIGS. 6 and 7 illustrate the amplitude and phase response of the interferometer, respectively, for fixed vibration velocity (i.e. for fixed frequency excursion). Measured at a CNR of 75 dB (3 kHz Bw), the amplitude is flat within 1 dB between 10 Hz and 20 kHz, and the 3 dB bandwidth is about 45 kHz. As shown in FIG. 7, the phase lag increases linearly with frequency, and the slope of the curve is −6.12°/kHz which corresponds to a delay of 17.0 μs.

Figure 8:
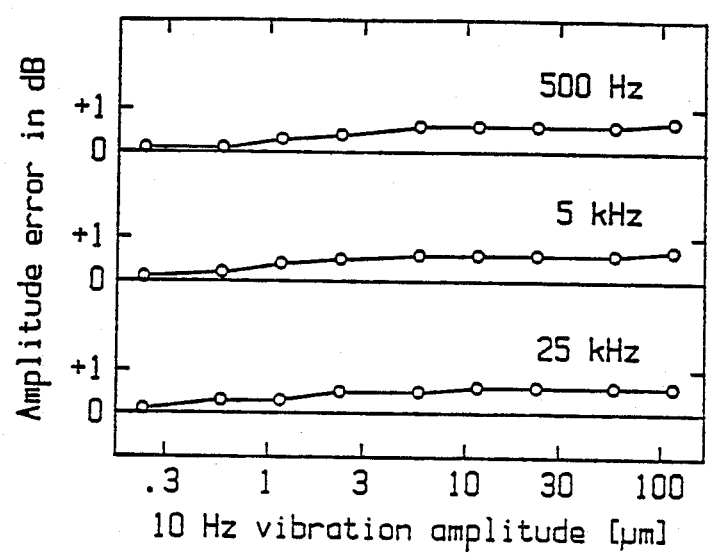
FIG. 8. Effect of low frequency disturbances on the accuracy of the amplitude measurements. Vibration amplitudes were measured at three different frequencies (500 Hz, 5 kHz, and 25 kHz) with and without a superimposed low frequency vibration (10 Hz). The relative difference between the measured vibration amplitudes with and without 10 Hz vibration is reported in dB as a function of the amplitude of the 10 Hz vibration.

Effect of low frequency vibrations on the accuracy of measurement:

In animal measurements, the small vibrations to be measured are always superimposed on large low frequency movements of the animal due to breathing and blood pulsations. These low frequency perturbations were simulated with a 10 Hz vibration. The error in measuring the amplitude of a vibrating object in the presence of a large low frequency movement was investigated. Results for three different vibration frequencies (500 Hz, 5 kHz, and 25 kHz) are given in FIG. 8. The vibration amplitude of the test object in each case was 30 dB above the noise floor simulating poor signal quality. This was equivalent to a vibration amplitude of $700 \cdot 10^{-12}$ m, $32 \cdot 10^{-12}$ m, and $6 \cdot 10^{-12}$ m at 500 Hz, 5 kHz, and 25 kHz, respectively. The error is given in dB versus the amplitude of the 10 Hz vibration. Even when these amplitudes are greater than 0.1 mm, the error is less than 0.7 dB. This experiment clearly demonstrates that the accuracy of the measurement is not appreciably affected by superimposed large amplitudes at low frequencies.

Figure 9:
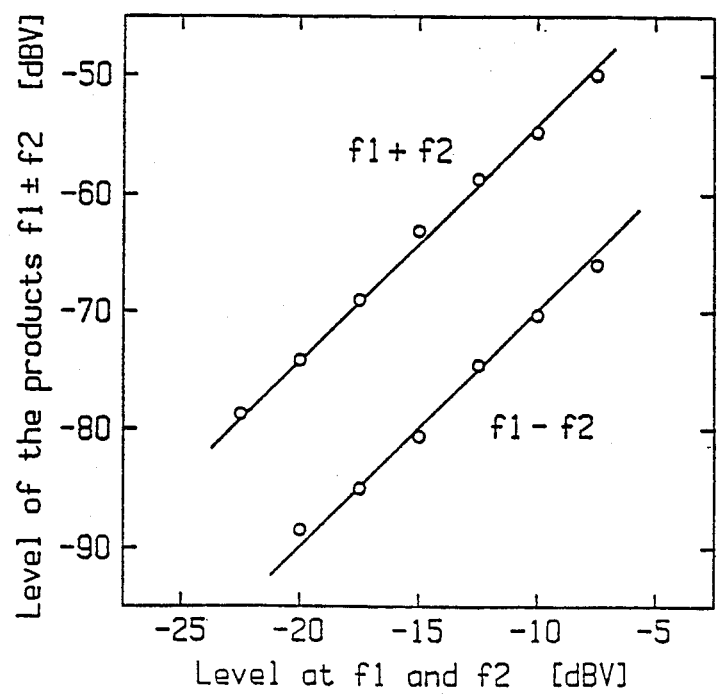
FIG. 9. Linearity of the interferometer levels of the intermodulation products $(f_1+f_2)$ and $(f_1-f_2)$ are shown as a function of the level of the fundamental vibrations at $f_1$ and $f_2$ (8 and 10 kHz). A level of $-15$ dBV corresponds to a vibration amplitude of $8.10-8$ m at each of the two frequencies.

Linearity of measurement:

The linearity of the interferometer was tested with two mirrors vibrating with the same amplitude at 8 kHz and 10 kHz (mirror M in FIG. 2 was also mounted on a vibrating system). As shown in FIG. 9, the amplitudes of the intermodulation products $(f_1+f_2)$ and $(f_1-f_2)$ were measured as a function of the vibration amplitude. Both amplitudes increase as the square of the vibration level (20 dB per 10 dB increase in vibration amplitude) in agreement with the fact that they are intermodulation products. For example, at a vibration level of $-15$ dBV (corresponding to an amplitude of $8 \cdot 10^{-8}$ m), the intermodulation products $(f_1+f_2)$ and $(f_1-f_2)$ have an amplitude of $-64$ dBV and $-80$ dBV, i.e. they are 49 dB and 65 dB below the output due to the 8 kHz or the 10 kHz vibration alone. Since the vibration measurements to be made with this instrument will be below $10^{-10}$ m, the nonlinear distortion is expected to be less than $-100$ to $-120$ dB.

Figure 10:
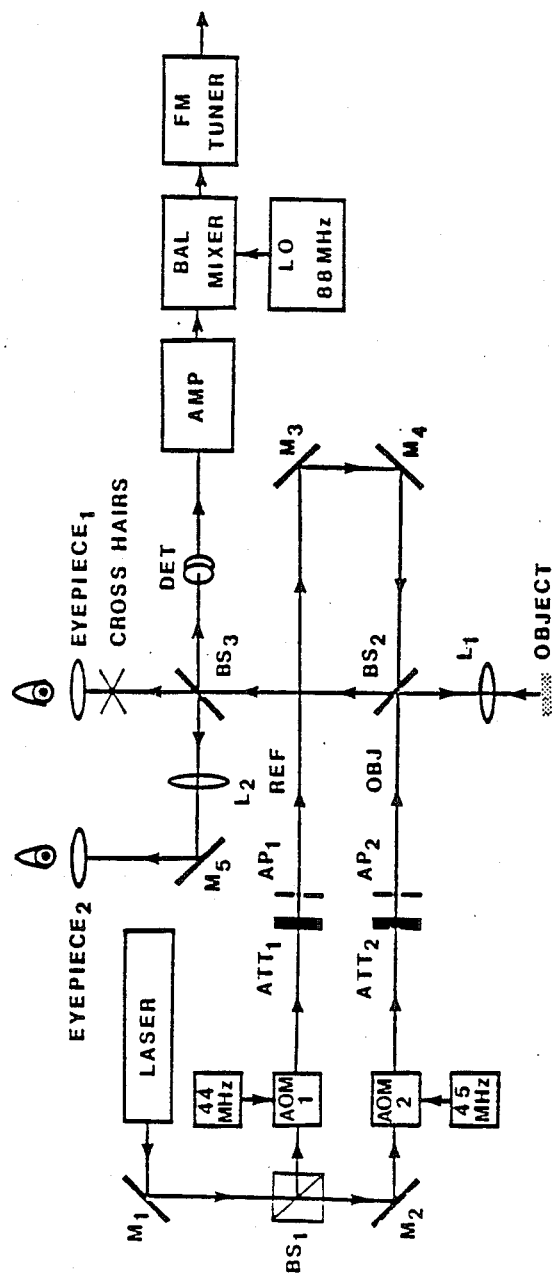
FIG. 10. Schematic of the heterodyne interferometer used for round window and basilar membrane vibration measurements.

Optical measuring system:

The optical arrangement used for testing the heterodyne interferometer in animal experiments is shown in FIG. 10. Details of the frequency shifting arrangement using acousto-optical modulators have been described earlier [51]. Due to frequency shifting the frequency difference between the object and the reference beam is 1 MHz. The object beam is deflected downwards by the beam splitter $BS_2$ and is brought to focus on the object by the lens $L_1$ (40 m, fl doublet). The light reflected from the object travels through the lens $L_1$, through the beam splitter $BS_2$ and falls on the detector after reflection from the beam splitter $BS_3$. The eye piece 1 with a cross hair is provided to visualize the object and to locate the position at which vibration measurement is made. A second eyepiece (2) allows viewing of the detector face and aids in the alignment of the object and reference beams.

The reference beam falls on the detector after reflections from mirrors $M_3$, $M_4$, and beam splitters $BS_2$, $BS_3$. The detector output is at 1 MHz. It is amplified using a low noise amplifier and frequency shifted to 89 MHz using a local oscillator and balanced mixer. The signal at 89 MHz is then demodulated using a high quality FM tuner (Revox B760). The receiver output is linearly proportional to the velocity of the object over a wide amplitude and frequency range (see [51] for details of the amplifier, mixer and receiver characteristics).

Signal analysis system:

To measure the vibration amplitude, the output of the FM tuner is amplified and fed to a Data General S/2000 Eclipse minicomputer via an anti-aliasing filter and an A/D converter. [50]. The averaging is carried out by accumulating the samples in 1024 consecutive time bins each of 14 μs width. The signal to noise ratio of the measurement is enhanced further by synchronously averaging 50 frames of response.

Surgical Preparation:

Healthy cats, weighing between 2.0 and 5.0 kg, with clean external ears, were selected for the experiments. The animals were given an intramuscular injection of chlorpromazine (14 mg per kg of body weight) and then anesthetized with an intraperitoneal injection of sodium pentobarbital (Nermbutal, 22 mg per kg of body weight). The anesthesia was maintained throughout the experiment by supplemental doses of pentobarbital (10% of original dose at intervals of about 2 h, if needed). The cat was tracheotomized, the top of the skull was exposed, and a head holder was cemented to the skull using dental cement. This improved the mechanical stability in holding the head. The bulla on the left side is opended to provide wide access to the round window.

The ear canal was cut short (4.5 mm length), and a metal ear insert in the shape of a hollow conical frustum was placed in the ear canal. The dimensions of the ear insert were chosen so that its front end rests against the body ridge around the external auditory meatus and its back end fits tightly into the cut ear canal. The angle of placement of the ear insert is adjusted so that its axis follows that of ear canal. The ear insert has a metal tab which is cemented to the skull with dental cement. This ensured that the ear insert would not move during the experiment and would stay in position after the acoustic transducer and sound delivery tube were pulled out. The insert defines a reference plane in the external auditory meatus for determining probe microphone position. Sound pressure is applied to the tympanic membrane via the acoustic system described above and its level is measured with a probe microphone that runs coaxially through the end of the sound tube [46,47,49]. The experiments are carried out inside a double walled IAC soundproof chamber. The interferometer is mounted on a vibration isolated table. The animal is placed in the interferometer. Its head is oriented so that the incident laser beam falls on the selected portion of the round window membrane and the reflected beam falls of the photodetector. The positioning is carried out with an x, y micromanipulator on which the head holder is mounted and the angular adjustments are made with the aid of two gimbel rings (for details of the x, y micromanipulator and the gimbel rings see [43]). Reference beam position and orientation is adjusted so that it overlaps with the object beam at the detector and the carrier to noise ratio at the output of the detector is maximized.

In measuring the round window vibrations resulting from the acoustic stimulation of the ear, two methods were employed:

i. Fixed SPL method. This consists of applying a specified constant SPL at the tympanic membrane at all frequencies and measuring the vibration amplitude and phase. This method is simple to implement. Interpretation of results however is complicated by the possibility that at some frequencies the signal may be below the noise level. It was shown earlier that the noise level of the heterodyne interferometer system varies with frequency. It rises steeply at lower frequencies [51. In order to ensure that there is adequate S/N ratio in the vibration measurements, it is necessary to measure the noise level in each experiment. The noise is measured exactly with the same procedure as the signal except that during the noise measurements there is no acoustical signal applied to the ear.

ii. Fixed S/N ratio method. In this method the vibration amplitude is measured at a level at which a specified S/N is maintained. First the noise level around the test frequency is measured. The signal level required to obtain the correct S/N ratio is calculated and the correct drive voltage is applied to the acoustic transducer. Vibration amplitude is measured with the interferometer and the actual S/N ratio is determined. If this ratio is within acceptable limits (Specified ratio±5 dB) the following set of parameters are recorded: (a) frequency; (b) drive voltage to the acoustic transducer; (c) attenuator setting in the driver system; (d) interferometer amplitude and phase; (e) interferometer noise level; (f) interferometer S/N ratio; and (g) vibration amplitude corresponding to the interferometer output. Measurement then proceeds to the next frequency. If the observed ratio is not within the acceptable limit the drive voltage is readjusted and the process is repeated until the desired S/N ratio is obtained. The complete process is automatically carried out by software. In measuring a linear system the correct S/N ratio is generally obtained in the first setting the drive voltage. In a non-linear system several settings may be necessary to obtain the desired S/N ratio. One complicating factor is that the magnitude of noise fluctuates over a wide range in successive measurements. To obtain a desired S/N ratio, many cycles of adjustment may be necessary. To minimize this problem the rms noise magnitude is averaged over five frequencies below and five above the measurement frequency. The frequency increment is 65 Hz, therefore the noise is averaged over a total frequency band of 650 Hz.

This method has the advantage that all the data is collected with constant S/N ratio. If the drive level required for the acoustic transducer to produce the Specified S/N ratio is too high and outside the dynamic range of the acoustic driving system, the measurement is not carried out and the frequency is skipped.

Measurements with constant SPL method:

Round window vibration amplitude is shown as a function of frequency in FIG. 11. These amplitudes were measured for a constant SPL at the tympanic membrane. Vibration levels were measured at five sound pressure levels 10 dB apart and with the sound turned off. Data measured at only to levels 60 dB and 40 dB is shown in FIG. 11 along with the noise level. The noise level is highest at very low frequencies, ($8 \times 10^{-10}$ m at 130 Hz), and it decreases rapidly to $1.4 \times 10^{-12}$ m as frequency increases to 6 kHz. Above 6 kHz the noise level is approximately flat with increasing frequency up to 30 kHz. For a SPL of 40 dB (dotted curve FIG. 11), the S/N ratio is 6 dB at 130 HZ. It increases to about 14 dB at 1 kHz and to about 20 dB at 4 kHz. Above 25 kHz the S/N ratio decreases again. It is clear that the S/N ratio is marginal both at low and high frequencies. Thus the measurements at or below 40 dB SPL will be unsatisfactory in the regions where S/N ratio is poor. The exact magnitude of the noise is not predictable in advance since it depends on several experimental variables. Therefore this method, although simple to implement, is inefficient because some of the data collected may not be usable.

Measurements with constant S/N ratio method:

In these measurements the noise level is measured first. It should be noted that the noise has been averaged over five consecutive frequencies above and below the frequency of measurement. The noise level measured as a function of frequency is shown in FIG. 12. The level is highest at low frequencies (400 Hz), and it decreases rapidly as frequency increases to 2 kHz. Above 2 kHz the level is approximately flat up to a frequency of 30 kHz.

Vibration amplitudes measured near the edge of the round window membrane as a function of frequency at 40 dB S/N ratio are shown in FIG. 12. The two curves run parallel to each other with a ratio of 40 dB. The measured vibration amplitude was approximately $5 \times 10^{-9}$ meters at 400 Hz and $3 \times 10^{-10}$ meters between 3 and 30 kHz. Measurements at the same spot on the round window membrane were also made with 20 dB S/N ratio (not shown in FIG. 12). In this case the measured amplitude was lower by a factor of 10, i.e. from $5 \times 10^{-10}$ meters to $3 \times 10^{-11}$ meters. Vibration measurements were repeated at the same spot as the first measurement described above after readjustment of the interferometer. These measurements are shown in FIG. 13. Since the noise level was higher in this case, the measurements were made at slightly higher level. In both experiments, the SPL at the eardrum was recorded and sound pressure level required to produce $10^{-10}$ meters vibration amplitude can be calculated assuming linearity. The plots for the two sets of measurements at 40 dB S/N ratio are shown in FIG. 14. The repeatability of these results is better than 1 dB in amplitude and 20° in phase.

Basilar membrane measurements:

This test was made to demonstrate that the heterodyne interferometer could be utilized to measure basilar membrane vibration without placing a mirror on it or altering its normal reflectivity. The experiments were made in a cadaver ear with perilymph drained from scala tympani so that the basilar membrane could be visualized. The orientation and position of the animal's head were adjusted so that the light reflected from the basilar membrane fell on the photodector. FIG. 15 shows the noise floor of the measuring system (dotted line) and the basilar membrane vibration amplitudes measured as a function of frequency at 60 dB SPL at the tympanic membrane. The vibration amplitude is $4 \times 10^{-9}$ m at 120 Hz and approximately $5 \times 10^{-9}$ m between 15 and 25 kHz. The noise level in the high frequency region is about $3 \times 10^{-12}$ m, therefore measurements can be made with good S/N ratio (20 dB) down to $10^{-10}$ m in the high frequency region. It is well known that basilar membrane vibration amplitude for a given SPL decreases in cadaver ears particularly in the CF region [14,18]. Therefore, in normal ears, the measurement sensitivity will be higher.

Discussion:

The first objective of these experiments was to test if the vibrations of the round window membrane could be measured with the heterodyne interferometer. Access to the membrane is simple but it has low optical reflectivity. It had not been possible to measure its vibrations using a homodyne interferometer because of this low reflectivity and the large low frequency excursions of the membrane. The measurements made in these experiments had five basic aims:

A. To test if vibrations of the round window membrane could be measured directly, without enhancing its reflectivity by external means such as placing a mirror. Measurements were made under conditions where the light levels reaching the detector were very similar to levels that would be obtained from the basilar membrane fluid interface. The light reaching the detector from the round window membrane was sufficient for the vibration measurements because the carrier to noise ratio (1 kHz bandwidth) at the input of the receiver was between 60 and 63 dB:

B. To test if accurate measurements could be made inspite of the low frequency excursions of the round window membrane. Two successive measurements of the round window vibration amplitude were made at the same spot. Both measurements were made with a S/N ratio of 40 dB. The high S/N ratio was used to minimize the effect of noise. These two sets of measurements show excellent repeatability, better than 1 dB throughout the frequency range used. If the accuracy of the measurements were affected by the low frequency movements of the membrane, then the results would vary in successive measurements. The spot at which these measurements were made was located at the edge of the round window membrane where it is steeply curved. It was therefore expected that the effect of low frequency movements would be pronounced in this region. The close repeatability of the results indicates that background movement does not affect the accuracy of measurement of the heterodyne interferometer. This is in agreement with theory and with results obtained in laboratory experiments;

C. To determine the noise level of the system. Noise level was measured when recording the mechanical response of the round window membrane with the heterodyne interferometer. The measurement bandwidth (3 dB) of the system was approximately 1.3 Hz. The equivalent vibration level corresponding to the noise level was $8 \times 10^{-10}$ m at 130 Hz and approximately $1.4 \times 10^{-12}$ m above 6 kHz. This noise level was measured with a signal to noise ratio of 60 dB (1 kHz BW) at the input of the receiver. Theoretical predictions of noise for 1.5 Hz bandwidth are $2 \times 10^{-10}$ at 100 Hz and $1.5 \times 10^{-12}$ m above 6 kHz. The noise measured above 6 kHz compares well with predicted performance, however there is considerable excess noise at low frequencies. This excess noise level is the same when recording from the basilar membrane in a cadaver preparation. Therefore the excess noise is not due to low frequency movements of the round window membrane;

D. To determine the vibration amplitude that could be measured with an adequate S/N ratio. It was shown that the round window vibrations could be measured with 20 dB S/N ratio at a level of $5 \times 10^{-10}$ meters at 400 Hz and at a level of $3 \times 10^{-11}$ meters above 2000 Hz. The effective measurement bandwidth was 1.3 Hz. The sensitivity of measurement is high and vibrations can therefore be measured at sound pressure levels as low as 20 dB;

E. To test if the basilar membrane vibrations could be measured without enhancing optical reflectivity by external means. It was shown that basilar membrane vibrations could be measured using the heterodyne interferometer in spite of its low optical reflectivity. The measurement sensitivity was $8 \times 10^{-9}$ m at 130 Hz and $6 \times 10^{-11}$ m above 2 kHz (20 dB S/N ratio). Vibrations can therefore be measured with high sensitivity at sound pressure levels approaching the threshold of hearing.

Conclusions:

The experiments described above have generated three principal findings: (a) vibration measurements can be carried out with a heterodyne interferometer directly on the round window and the basilar membranes utilizing their natural reflectivity; (b) these measurements can be made at very low vibration amplitudes with good S/N ratio; and (c) the amplitude and phase measurements show excellent repeatability and they are not sensitive to the large low frequency excursions of the round window membrane.

References

1. Gundersen, T., Skarstein, O., and Sikkeland, T. (1978), "A study of the vibration of the basilar membrane in human temporal bone preparations by the use of the Mossbauer effect", *Acta. Otolaryngol.* 86, 225-232.
2. Helfenstein, W. M. (1973), "Beitrag zur Messung der akustisch bedingten Bewegungen und Identifikation des mechanischen Teils des Innenohrs der Katze", Ph.D. thesis (Eidgenossischen Technischen Hochschule, Zurich, Switzerland).
3. Johnstone, B. M., and Boyle, A. J. F. (1967), "Basilar membrane vibrations examined with the Mossbauer technique", *Science* 158, 390-391.
4. Johnstone, B. M., Taylor, K. J., and Boyle, A. J. (1970), "Mechanics of the Guinea pig cochlea", *J. Acoust. Soc. Am.* 47, 504-509.
5. Johnstone, B. M., and Yates, G. K. (1974), "Basilar membrane tuning curves in the Guinea pig", *J. Acoust. Soc. Am.* 55, 584-587.
6. Peake, W. R., and Ling, A., Jr. (1980), "Basilar membrane motion in the alligator lizard: Its relation to tonotopic organization and frequency selectivity", *J. Acoust. Soc. Am.* 67, 1736-1745.
7. Robles, L., and Rhode, W. S. (1974), "Nonlinear effects in the transient response of the basilar membrane" in "Facts and models in hearing", Eds. E. Zwicker and E. Terhardt, Springer Verlag, New York.
8. Robles, L., Ruggero, M. A., and Rich, N. C. (1985), "Mossbauer measurements of the mechanical response to single-tone and two-tone stimuli at the base of the chinchilla cochlea" in "Peripheral Auditory Mechanisms", Eds. J. B. Allen, J. L. Hall, A. Hubbard, S. T. Neely and A. Tubis, Springer Verlag, New York.
9. Rhode, W. S. (1971), "Observations of the vibration of the basilar membrane in squirrel monkey using the Mossbauer technique", *J. Acoust. Soc. Am.* 49, 1218-1231.
10. Rhode, W. S. (1973), "An investigation of the post-mortem cochlear mechanics using the Mossbauer effect" in "Basic Mechanics in Hearing", Acad. Press, New York, pp. 49-67.
11. Rhode, W. S. (1974), "Measurement of vibration of the basilar membrane in the squirrel monkey", Annals of Otology, Rhinol. & Laryngol. 83, 619.
12. Rhode, W. S. (1977), "Some observations of two-tone interactions measured using the Mossbauer effect" in "Psychophysics and Physiology of Hearing", Eds. E. F. Evans and J. P. Wilson, Academic Press, London, pp 27-38.
13. Rhode, W. S. (1978), "Some observations on cochlear mechanics", *J. Acoust. Soc. Am.* 67, 158-176.
14. Sellick P. M., Patuzzi, R., and Johnstone, B. M. (1982), "Measurement of basilar membrane motion in the Guinea pig using the Mossabauer technique", *J. Acoust. Soc. Am.* 72, 131-141.
15. Wilson, J. P., and Johnstone, J. R. (1972), "Capacitive probe measures of basilar membrane vibrations" in "Symposium on Hearing Theory", *IPO Eindhoven*, the Netherlands, pp. 172-181.
16. Wilson, J. P. (1973), "A sub-miniature capacitive probe for vibration measurements of the basilar membrane", *J. Sound & Vibration* 30, 483-493.

17. Wilson, J. P., and Johnstone, J. R. (1975), "Basilar membrane and middle ear vibration in Guinea pig measured by capacitive probe", *J. Acoust. Soc. Am.* 57, 705–723.
18. Khanna, S. M., and Leonard, D. G. B. (1982), "Basilar membrane tuning in the cat cochlea", *Science* 215, 305–306.
19. Khanna, S. M. (1985), "Homodyne interferometer for basilar membrane vibrations measurements", *Hearing Res.* (in press).
20. Albe, F., Schwab, J., Smigielski, P., and Dancer, A. (1982), "Displacement measurement of the basilar membrane in Guinea pigs by means of an optical-fiber interferometer" in "Optics in Biomedical Sciences", Eds. G. von Bally and P. Greguss, Springer Verlag, Berlin, Heidelberg, New York, pp. 92–95.
21. Nokes, M. A., Hill, B. C., and Barelli, A. E. (1978), "Fiber optic heterodyne interferometer for vibration measurements in biological systems", *Rev. Sci. Instrum.* 49, 722–728.
22. Neiswander, P., and Slettemoen, G. A. (1981), "Electronic speckle pattern interferometric measurements of the basilar membrane in the inner ear", *Applied Optics* 20, 4271–4276.
23. Kelly, J. P., and Khanna, S. M. (1984a), "Ultrastructural changes in cochleas used for studies of basilar membrane mechanics", *Hearing Res.* 14, 59–78.
24. Kelly, J. P., and Khanna, S. M. (1984b), "Distribution of cochlear damage caused by the removal of the round window membrane", *Hearing Res.* 16, 109–126.
25. Leonard, D. G. B., and Khanna, S. M. (1984), "Histological evaluation of damage in cat cochlea used for measurement of basilar membrane mechanics", *J. Acoust. Soc. Am.* 75, 515–527.
26. Khanna, S. M., and Leonard, D. G. B. (1986), "Measurement of basilar membrane vibrations and evaluation of cochlear conditions", *Hearing Res.* 23:37–53.
27. Engstrom, H., Ades, H. W., and Hawkins, J. E., Jr. (1962), "Structure and function of the sensory hairs of the inner ear", *J. Acoust. Soc. Am.* 34, 1356.
28. Engstrom, H., Ades, H. W., and Andersson, A. (1966), "Structural Pattern of the Organ of Corti", Stockholm, Almquiist & Wiksell.
29. Engstrom, H., and Ades, H. W. (1972), "The ultrastructure of the cochlea" in "Ultrastructure of Animal Tissues and Organs", Eds. I. Friedman, Amsterdam, North-Holland Publ. Co.
30. Engstrom, H., and Engstrom, B. (1978), "Structure of the hairs on cochlear sensory cells", *Hearing Res.* 1, 49–66.
31. Flock, A., Kimura, R., Lundquist, P. G., and Wersall, J. (1962), "Morphological basis of directional sensitivity of the outer hair cells in the organ of Corti", *J. Acoust. Soc. Am. Suppl.* 34, 1351.
32. Koester, C. J. (1980), "Scanning mirror microscope with optical sectioning characteristics: Applications in Opthalmology", *Appl. Optics* 19, 1749–1757.
33. Liberman, M. C. (1982), "The cochlear frequency map for the cat: Labeling auditory nerve fibers of known characteristic frequency", *J. Acoust. Soc. Am.* 72, 1441–1449.
34. Flock, A., and Strelioff, D. (1984), "Graded and nonlinear mechanical properties of sensory hair in the mammalian hearing organ", *Nature* 310, 597–599.
35. Crane, R. (1969), "New developments in interferometry. V. Interference phase measurement", *Appl. Optics* 8, 538–542.
36. Dandliker, R. (1980), "Heterodyne holographic interferometry" in "Progress in Optics, Vol. XVII", Ed. E. Wolf, North-Holland, Amsterdam, pp. 1–84.
37. Dandliker, R., and Willemin, J. F. (1981), "Measuring microvibrations by heterodyne speckle interferometry", *Opt. Lett.* 6, 165–167.
38. Yariv, A., "Introduction to Optical Electronics", Second Edition, Holt, Rinehart and Winston, New York, pp. 271–287.
39. Wilemine, J. F. (1983), "Interferometric heterodyne de speckles: Applications a la mesure de vibrations mechaniques microscopiques", Ph.D. thesis (University of Neuchatel, Switzerland).
40. e.g. Drain, L. E. (1980), "The laser Doppler technique", Wiley, N.Y.
41. Panter, P.F., "Modulation, Noise, and Spectral Analysis applied to Information Transmission", McGraw-Hill Book Company, 1965, pp. 427–460.
42. Funnell, W. R. J., Decraemer, W. F. & Khanna, S. M. (1986), "On the damped frequency response of a finit-element model of the cat eardrum" Sub. JASA.
43. Khanna, S. M., Johnson, G. A., & Jacobs, J. (1986), "Homodyne interferometer for basilar membrane vibrations measurements", II-Hardware and Technique, *Hearing Res.* 23: 27–36.
44. Khanna, S. M., Tonndorf, J., and Walcott, W. W. Laser interferometer for the measurement of submicroscopic displacement amplitudes and their phases in small biological structures. *J. Acoust. Soc. Am.* 44: 1555–1565, 1968.
45. Khanna, S. M. and Leonard, D. G. B. Basilar membrane response measured in damaged cochleas of cats. In: *Mathematical Modeling of the Hearing Process* (Holmes, M. H. and Rubenfeld, L. A., eds.), Springer-Verlag, New York, pp. 70–84 1981.
46. Khanna, S. M. & Stinson, M. R. (1985), "Specification of the acoustical input to the ear at high frequencies", *J. Acoust. Soc. Am.* 77: 577–589.
47. Khanna, S. M. & Stinson, M. R. (1986), "Sound pressure distributions in the ear canals of cats", Procd. of 12th ICA, Toronto, Canada.
48. Khanna, S. M. Inner ear function based on the mechanical tuning of the hair cell. In: *Developments in the Hearing Science* (Berlin, C., ed.), College Hill Press, Calif., (in press), 1984.
49. Sokolick, W. G. (1977), "Improved acoustic system for auditory research", *J. Acoust. Soc. Am.* 62 Suppl. 1, S12.
50. Teich., M. C. & Khanna, S. M. (1985), "Pulse-number distribution for the neural spike train in the cat's auditory nerve", *J. Acoust. Soc. Am.* 77: 1110–1128.
51. Willemin, J. F., Dandliker, R. & Khanna, S. M. (1986), "Heterodyne interferometer for submicroscopic vibration measurements in the inner ear", Sub. JASA.

What is claimed is:

1. A heterodyne interferometer for measuring the amplitude of vibration of a vibrating object which comprises:
   (a) a laser for emitting a monochromatic light wave;
   (b) a beam splitter for splitting the light wave into an object light wave and a reference light wave, each having the same frequency;
   (c) a modulator for changing the frequency of the object light wave and the reference light wave so as to produce a predetermined offset between the frequency of the object light wave and the frequency of the reference light wave, said modulator being so positioned with respect to the beam splitter that the object light wave and the reference light wave pass through the modulator thereby changing their frequencies;

(d) means for directing the object light wave onto the vibrating object, said means so positioned between the object and the modulator that at least a portion of the object light wave is directed onto and reflected off of the object;

(e) a photodetector for producing, at a frequency equal to the predetermined offset, a beat signal varying in accordance with variations in the interference resulting from combining at least a portion of the reflected object light wave and the reference light wave wherein the power of the reference light wave is greater than the power of the portion of the reflected object light wave, the photodetector being so positioned with respect to the object and the beam splitter that it detects and measures the interference; and (f) means for processing the beat signal to measure variations in its phase or amplitude, said means being electrically connected to the photodetector in order to receive the beat signal.

2. The interferometer of claim 1, wherein the modulator comprises a first modulator on the object light wave and a second modulator on the reference light wave.

3. An interferometer of claim 2, wherein the first modulator and the second modulator each comprises an acousto-optical modulator.

4. An interferometer of claim 3, wherein the two modulators are driven by predetermined frequencies which differ by the predetermined offset.

5. An interferometer of claim 1, wherein the modulator comprises an acousto-optical modulator.

6. An interferometer of claim 1, wherein the means of directing the object light wave onto the object comprises an optical instrument.

7. An interferometer of claim 1, wherein the photodetector comprises a PN junction photodiode.

8. An interferometer of claim 7, wherein the photodiode is a silicon photodiode.

9. An interferometer of claim 1, wherein the photodetector comprises a photomultiplier tube.

10. An interferometer of claim 1, wherein the photodetector comprises a photoconductive device.

11. An interferometer of claim 1, wherein the means of processing the beat signal comprises a phase tracking system.

12. An interferometer of claim 1, wherein the means of processing the beat signal comprises a frequency demodulator.

13. An interferometer of claim 12, wherein the demodulator is an FM-demodulator.

14. An interferometer of claim 13, wherein the FM-demodulator comprises an FM-receiver.

* * * * *